United States Patent
Yoo et al.

(10) Patent No.: US 10,118,005 B2
(45) Date of Patent: Nov. 6, 2018

(54) DELIVERY SYSTEM

(71) Applicant: Wake Forest University Health Sciences, Winston-Salem, NC (US)

(72) Inventors: James J. Yoo, Winston-Salem, NC (US); Anthony Atala, Winston-Salem, NC (US); Kyle W. Binder, Winston-Salem, NC (US); Mohammad Z. Albanna, Winston-Salem, NC (US); Weixin Zhao, Winston-Salem, NC (US); Dennis Dice, Yadkinville, NC (US); Tao Xu, El Paso, TX (US)

(73) Assignee: WAKE FOREST UNIVERSITY HEALTH SCIENCES, Winston-Salem, NC (US)

( * ) Notice: Subject to any disclaimer, the term of this patent is extended or adjusted under 35 U.S.C. 154(b) by 0 days.

(21) Appl. No.: 14/019,714

(22) Filed: Sep. 6, 2013

(65) Prior Publication Data
US 2014/0012225 A1 Jan. 9, 2014

Related U.S. Application Data

(63) Continuation of application No. PCT/US2012/027731, filed on Mar. 5, 2012.
(Continued)

(51) Int. Cl.
*A61M 11/00* (2006.01)
*A61B 5/00* (2006.01)
(Continued)

(52) U.S. Cl.
CPC .......... *A61M 11/00* (2013.01); *A61B 5/0064* (2013.01); *A61B 5/1077* (2013.01);
(Continued)

(58) Field of Classification Search
CPC ..... A61M 11/00; A61M 35/00; A61B 5/0064; A61B 5/6835; A61B 5/1077;
(Continued)

(56) References Cited

U.S. PATENT DOCUMENTS

| | | |
|---|---|---|
| 3,830,228 A | 8/1974 | Foner |
| 4,727,494 A | 2/1988 | Buote |

(Continued)

FOREIGN PATENT DOCUMENTS

| | | |
|---|---|---|
| EP | 1459782 A2 | 9/2004 |
| WO | WO 2008/124126 A1 | 10/2008 |

(Continued)

OTHER PUBLICATIONS

Scientific American, Jesse Emspak Author, Jun. 17, 2010 Publication Date, Title: Desktop Printer Technology Used to Lay Down Regenerated Skin Cells to Treat Burns in Mice.*
(Continued)

*Primary Examiner* — Lynne Anderson
*Assistant Examiner* — Joseph D Boecker
(74) *Attorney, Agent, or Firm* — Myers Bigel, P.A.

(57) ABSTRACT

Provided herein is a delivery system, including: (a) an optical sensor configured to detect data to create a map of a patient bodily surface; and (b) a dispenser operatively associated with the optical sensor and configured to deliver compositions (optionally including cells) to the patient bodily surface based upon the data or map. Methods of forming a tissue on a patient bodily surface of a patient in need thereof are also provided, as are methods, systems and computer program products useful for processing patient bodily surface data.

22 Claims, 14 Drawing Sheets

Related U.S. Application Data

(60) Provisional application No. 61/450,021, filed on Mar. 7, 2011, provisional application No. 61/507,416, filed on Jul. 13, 2011.

(51) Int. Cl.

| | | |
|---|---|---|
| *A61B 5/107* | (2006.01) | |
| *A61M 35/00* | (2006.01) | |
| *A61L 27/22* | (2006.01) | |
| *A61L 27/24* | (2006.01) | |
| *A61L 27/38* | (2006.01) | |
| *A61L 27/60* | (2006.01) | |
| *C12N 5/077* | (2010.01) | |
| *B41J 3/407* | (2006.01) | |
| *A61B 17/00* | (2006.01) | |
| *A61B 17/322* | (2006.01) | |
| *A61B 90/50* | (2016.01) | |
| *A61B 34/30* | (2016.01) | |
| *A61B 34/10* | (2016.01) | |

(52) U.S. Cl.
CPC ............. *A61B 5/1079* (2013.01); *A61B 5/445* (2013.01); *A61B 5/6835* (2013.01); *A61L 27/225* (2013.01); *A61L 27/24* (2013.01); *A61L 27/3813* (2013.01); *A61L 27/60* (2013.01); *A61M 35/00* (2013.01); *C12N 5/0656* (2013.01); *A61B 34/30* (2016.02); *A61B 90/50* (2016.02); *A61B 2017/00969* (2013.01); *A61B 2017/3225* (2013.01); *A61B 2034/105* (2016.02); *B41J 3/4073* (2013.01)

(58) Field of Classification Search
CPC . A61B 5/1079; A61B 5/445; A61B 2034/105; A61B 90/50; A61B 2017/00969; A61B 2017/3225; A61B 34/30; C12N 5/0656; A61L 27/24; A61L 27/3813; A61L 27/60; A61L 27/225; B41J 3/4073
USPC ........... 604/289, 290; 250/234, 559.21, 235; 356/128, 607; 435/174, 397, 395, 101, 435/179, 377; 427/337, 338, 340; 424/93.7
See application file for complete search history.

(56) References Cited

U.S. PATENT DOCUMENTS

| | | | |
|---|---|---|---|
| 4,738,425 A | 4/1988 | Foster | |
| 5,355,439 A | 10/1994 | Bernstein et al. | |
| 5,536,084 A | 7/1996 | Curtis et al. | |
| 5,685,821 A | 11/1997 | Pike | |
| 5,696,887 A | 12/1997 | Bernstein et al. | |
| 5,702,444 A | 12/1997 | Struthers et al. | |
| 5,709,854 A | 1/1998 | Griffith-Cima et al. | |
| 5,716,404 A | 2/1998 | Vacanti et al. | |
| 5,776,050 A | 7/1998 | Chen et al. | |
| 5,971,976 A | 10/1999 | Wang et al. | |
| 6,055,704 A | 5/2000 | Leibman | |
| 6,165,487 A | 12/2000 | Ashkar et al. | |
| 6,201,065 B1 | 3/2001 | Pathak et al. | |
| 6,205,243 B1 | 3/2001 | Migdal et al. | |
| 6,381,026 B1 | 4/2002 | Schiff et al. | |
| 6,428,802 B1 | 8/2002 | Atala | |
| 6,438,272 B1 | 8/2002 | Huang et al. | |
| 6,482,435 B1 | 11/2002 | Stratton et al. | |
| 6,537,567 B1 | 3/2003 | Niklason et al. | |
| 6,562,326 B1 | 5/2003 | Miller | |
| 6,589,728 B2 | 7/2003 | Csete et al. | |
| 6,676,654 B1 | 1/2004 | Balle Petersen et al. | |
| 6,783,964 B2 | 8/2004 | Opara | |
| 6,788,210 B1 | 9/2004 | Huang et al. | |
| 6,856,407 B2 * | 2/2005 | Knighton | G06T 7/0057 356/601 |
| 6,923,833 B2 | 8/2005 | Wasielewski | |
| 6,969,480 B2 | 11/2005 | Dalton et al. | |
| 6,986,739 B2 | 1/2006 | Warren et al. | |
| 6,991,652 B2 | 1/2006 | Burg | |
| 6,995,013 B2 | 2/2006 | Connelly et al. | |
| 7,019,192 B2 | 3/2006 | Gertzman et al. | |
| 7,051,654 B2 | 5/2006 | Boland et al. | |
| 7,150,989 B2 | 12/2006 | Goldman et al. | |
| 7,630,089 B2 | 12/2009 | Babayoff et al. | |
| 7,643,025 B2 | 1/2010 | Lange | |
| 7,705,291 B2 * | 4/2010 | Al-Moosawi et al. | ....... 250/234 |
| 2003/0100824 A1 | 5/2003 | Warren et al. | |
| 2003/0170285 A1 | 9/2003 | Veazey et al. | |
| 2003/0175410 A1 * | 9/2003 | Campbell | A61L 27/38 427/2.24 |
| 2004/0053869 A1 | 3/2004 | Andrews et al. | |
| 2004/0115810 A1 | 6/2004 | Luu et al. | |
| 2004/0161412 A1 | 8/2004 | Penn et al. | |
| 2004/0214319 A1 | 10/2004 | Pebay et al. | |
| 2004/0237822 A1 | 12/2004 | Boland et al. | |
| 2004/0241856 A1 | 12/2004 | Cooke | |
| 2004/0253365 A1 * | 12/2004 | Warren | A61B 5/0066 427/2.1 |
| 2005/0054893 A1 | 3/2005 | Atala et al. | |
| 2005/0124003 A1 | 6/2005 | Atala et al. | |
| 2005/0131212 A1 | 6/2005 | Sieg et al. | |
| 2005/0153941 A1 | 7/2005 | Miyabayashi et al. | |
| 2005/0202428 A1 | 9/2005 | Andrews et al. | |
| 2005/0227353 A1 | 10/2005 | Mummery | |
| 2005/0237581 A1 | 10/2005 | Knighton et al. | |
| 2005/0266553 A1 | 12/2005 | Pebay et al. | |
| 2006/0006018 A1 | 1/2006 | Fleming et al. | |
| 2006/0013804 A1 | 1/2006 | Megency et al. | |
| 2006/0156978 A1 | 7/2006 | Lipson et al. | |
| 2007/0031384 A1 | 2/2007 | Atala et al. | |
| 2007/0169307 A1 | 7/2007 | Yu et al. | |
| 2008/0033410 A1 | 2/2008 | Rastegar et al. | |
| 2008/0070304 A1 | 3/2008 | Forgacs et al. | |
| 2009/0117087 A1 * | 5/2009 | Carroll | A61L 27/38 424/93.7 |
| 2009/0118600 A1 | 5/2009 | Ortiz et al. | |
| 2009/0208466 A1 * | 8/2009 | Yoo et al. | ..................... 424/93.7 |
| 2009/0208577 A1 | 8/2009 | Xu et al. | |
| 2010/0160183 A1 * | 6/2010 | Xu et al. | ........................ 506/30 |
| 2011/0212501 A1 * | 9/2011 | Yoo | ..................... 435/174 |
| 2011/0280914 A1 * | 11/2011 | Prestwich | A61L 27/38 424/400 |
| 2013/0017564 A1 * | 1/2013 | Guillemot | B01L 3/0268 435/8 |
| 2014/0012225 A1 | 1/2014 | Yoo et al. | |
| 2015/0224226 A1 * | 8/2015 | Bhatia | C12N 5/0068 435/1.1 |
| 2015/0246072 A1 * | 9/2015 | Bhatia | A61L 27/18 424/93.7 |
| 2015/0366655 A1 * | 12/2015 | Tumey | B29C 67/0088 623/15.12 |
| 2016/0115457 A1 * | 4/2016 | Kim | A61L 27/60 435/29 |
| 2016/0122723 A1 * | 5/2016 | Retting | C12N 5/0698 435/366 |
| 2017/0130192 A1 * | 5/2017 | Retting | C12N 5/0062 |
| 2017/0136147 A1 * | 5/2017 | Tumey | B29C 67/0085 |
| 2017/0218228 A1 * | 8/2017 | Jose | C09D 175/06 |

FOREIGN PATENT DOCUMENTS

| | | |
|---|---|---|
| WO | WO 2008/153968 A2 | 12/2008 |
| WO | WO 2010/030964 A2 | 3/2010 |
| WO | WO 2011/085225 A1 | 7/2011 |

OTHER PUBLICATIONS

Scientific American Article "Desktop PRinter Used to Lay Down Regenerated Skin Cells to Treat Burn Mice" Jesse Emspak author, dated Jun. 17, 2010.*

(56) References Cited

OTHER PUBLICATIONS

Xu, Tao and Yuan, Yuyu and Yoo, James J., "Cell Source for Tissue and Organ Printing", "Printed Biomaterials: Novel Processing and Modeling Techniques for Medicine and Surgery", editor Narayan, Roger and Boland, Thomas and Lee, Yuan-Shin, 2010, Springer New York, New York, NY, p. 57-69; retrieved from https://link.springer.com/chapter/10.1007.*

Extended European Search Report, EP 12754610.0, dated Aug. 22, 2014.

Binder KW et al. Development of a novel delivery device for in situ bioprinting of the skin. Termis-Americas 2010 Orlando Conference. Dec. 5, 2010, 1 page.

Binder KW et al. Drop-on-demand inkjet bioprinting: a primer. Gene Therapy and Regulation. Mar. 1, 2011; 6(1): 33-49.

Skardal A et al. Bioprinted amniotic fluid-derived stem cells accelerate healing of large skin wounds. Stem Cells Translational Medicine. 2012; 1: 792-802.

Fox M. Inkjet-like device 'prints' cells right over burns. reuters.com/articles/2010/04/08/us-wounds-printer-idUSTRE63657520100408. Retrieved from Internet Jun. 8, 2015, 1 p.

Binder KW. Doctoral Dissertation: In situ bioprinting of the skin. Wake Forest University Graduate School of Arts and Sciences, Molecular Genetics and Genomics. May 2011; 463 pp.

Binder KW et al. Poster presentation, "In situ bioprinting of the skin for burns." 2009 Tissue Engineering and Regenerative Medicine International Society World Congress, dated Aug. 31-Sep. 3, 2009, 9 pp.

European Patent Office Examination Report, EP 12754610.9, dated Jul. 1, 2015.

European Patent Office Examination Report, EP 12754610.9, dated Nov. 9, 2015.

Korean Intellectual Property Office Notice of Preliminary Rejection, KR 10-2012-7020050, dated Feb. 15, 2017.

International Search Report and Written Opinion, PCT/US2012/027731, dated Jul. 13, 2012.

Grant, I. et al., "The co-application of sprayed cultured autologous keratinocytes and autologous fibrin sealant in a porcine wound model", *British Journal of Plastic Surgery*, 2002, vol. 55, pp. 219-227.

International Preliminary Report on Patentability Corresponding to International Application No. PCT/US2012/027731; dated Sep. 19, 2013; 11 Pages.

International Preliminary Report on Patentability Corresponding to International Application No. PCT/US2011/020551; dated Jul. 19, 2012; 9 Pages.

International Search Report and Written Opinion, PCT/US12/27731, dated Jul. 13, 2012.

International Search Report Corresponding to International Application No. PCT/US2011/020551; dated May 25, 2011; 12 Pages.

Pardo et al., "Characterization of Patterned Self-Assembled Monolayers and Protein Arrays Generated by the Ink-Jet Method", *Langmuir*, 2003, vol. 19, pp. 1462-1466.

Supplementary European Search Report, EP11732221, dated Jun. 5, 2013.

Wilson et al., "Cell and Organ Printing 1: Protein and Cell Printers", *The Anatomical Record Part A*, 272A, 2003, pp. 491-496.

Korean Intellectual Property Office Notice of Preliminary Rejection, KR 10-2013-7025987, dated May 18, 2018, 9 pages, English translation, 7 pages.

* cited by examiner

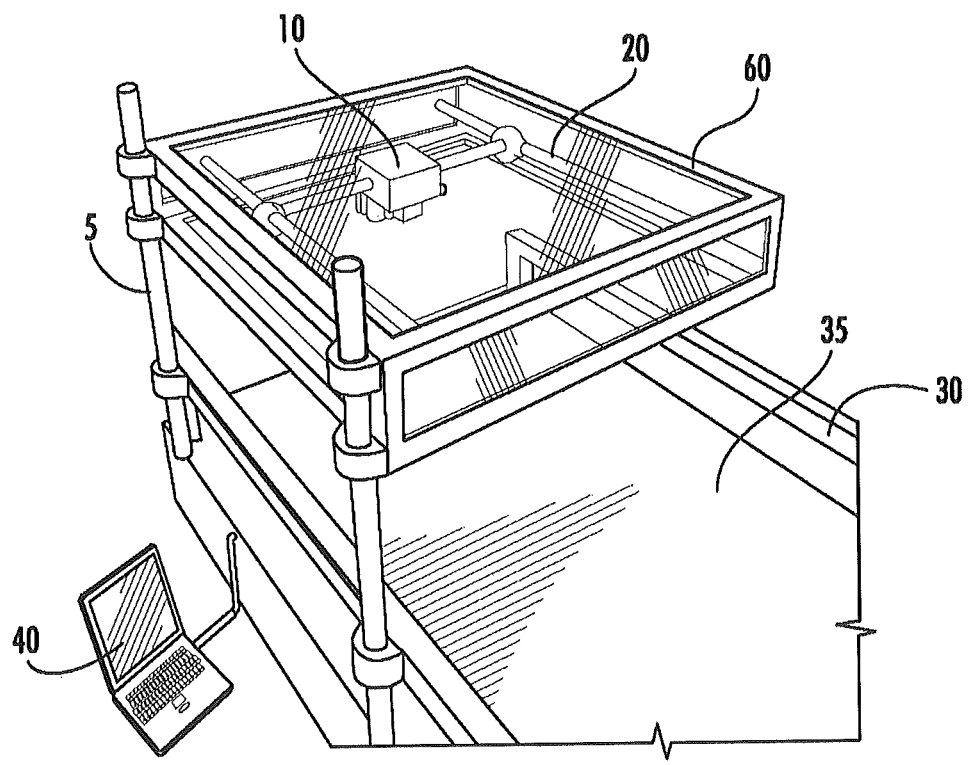
FIG. 6
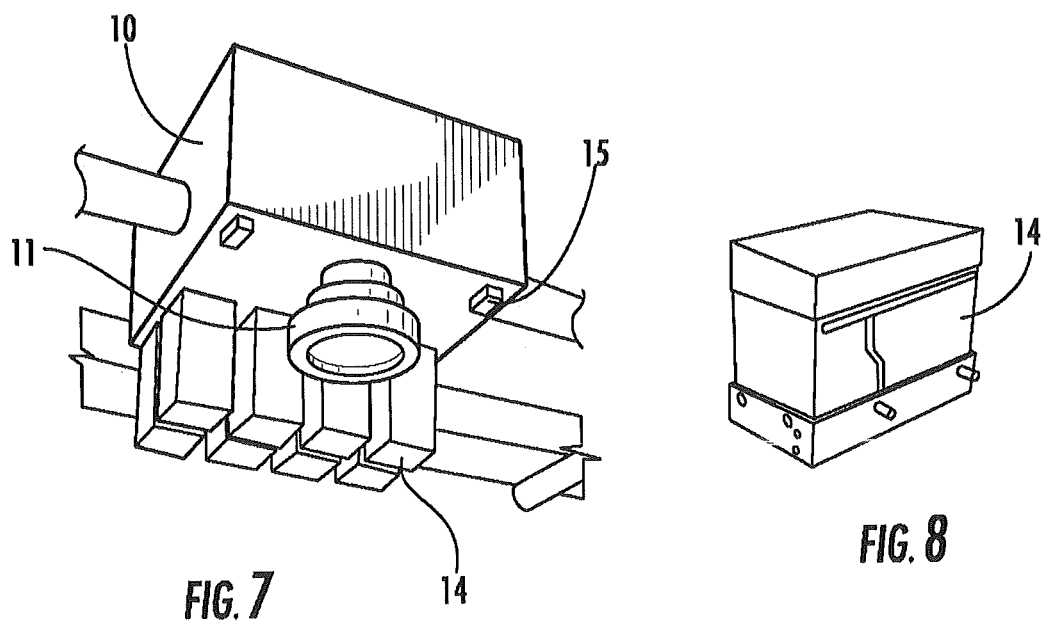
FIG. 7
FIG. 8

DELIVERY SYSTEM

RELATED APPLICATIONS

This application is a continuation under 35 U.S.C. 111(a) of PCT Application No. PCT/US2012/027731, filed Mar. 5, 2012, which in turn claims the benefit under 35 U.S.C. § 119(e) of U.S. Provisional Patent Application No. 61/450,021, filed Mar. 7, 2011, and U.S. Provisional Patent Application No. 61/507,416, filed Jul. 13, 2011, the contents of each of which is incorporated by reference herein in its entirety.

This application is related to U.S. patent application Ser. No. 12/986,812, filed Jan. 7, 2011, and published on Jul. 14, 2011, as Publication No. US 2011/0172611, the contents of which is incorporated by reference herein in its entirety.

STATEMENT OF GOVERNMENT SUPPORT

This work was supported by grant W81XWH-08-2-0032 from the Armed Forces Institute for Regenerative Medicine. The U.S. Government has certain rights in this invention.

FIELD OF THE INVENTION

The present invention concerns the in situ delivery of viable cells onto a subject.

BACKGROUND OF THE INVENTION

In the United States, the mortality rate for burns is approximately 4.9% and increases dramatically with increasing total body surface area (TBSA) burned. The gold standard of treatment is the split-thickness autograft, but this technique requires injuring one or more sites of undamaged skin. Other treatment techniques include silver sulfadiazine, INTEGRA® (Johnson and Johnson, Hamburg, Germany; Integra Life Sciences Corporation, NJ), BIOBRANE® (Dow Hickam/Bertek Pharmaceuticals, Sugar Land, Tex.), TRANSCYTE® (Advanced Tissue Sciences, Inc., La Jolla, Calif.), and allogeneic cells.

Large-scale manufacturing processes necessitate production of standard sizes of skin substitutes, but these standard-sized products cannot adequately cover irregular wounds. In addition, nearly all of these techniques require multiple surgical procedures, and are not ideal for large body surface area burns.

Allogeneic cell therapy can eliminate the need for autologous cell culture. Current delivery techniques include spraying cells onto the patient or seeding a scaffold with cells before implantation. Cell spraying has been used to treat burns with autologous fibroblasts and keratinocytes, but the delivery precision of current spraying technology is low.

The ideal skin substitute possesses the following qualities: (1) it adheres intimately to the wound bed, especially for irregular surfaces; (2) it provides a non-antigenic microbial barrier; (3) it participates in normal host repair mechanisms; (4) it maintains elasticity and long-term durability; (5) it displays long-term mechanical and cosmetic function comparable to split-thickness autografts; (6) it requires a single surgical procedure; (7) it is inexpensive; (8) it has an indefinite shelf life; and (9) it has minimal storage requirements.

New treatments are needed that better address the needs of burn wound patients, as well as patient having other wounds and tissue injury or disease.

SUMMARY OF THE INVENTION

Provided herein is a delivery system including a control module configured to generate a map of a patient bodily surface based on patient bodily surface data captured by a scanning system and to generate a command to operate a dispensing system to deliver cells and/or compositions to the patient bodily surface based on the map. In some embodiments, the delivery system also includes a database including scanning system parameters and/or dispensing system parameters stored therein. In some embodiments, the delivery system further includes an interface module configured to convert the patient bodily surface data into a format suitable for use by the control module to generate the map based on the scanning system parameters and/or to format the command to operate the dispensing system to deliver the cells and/or compositions based on the dispensing system parameters.

Also provided is a delivery system, including: (a) an optical sensor configured to detect data used to create a map of a patient bodily surface; and (b) a dispensing system operatively associated with the optical sensor and configured to deliver cells and/or compositions to the patient bodily surface based upon the map. In some embodiments, the sensor and dispensing system (or a portion thereof) can be associated with one another by connection of each to a common support or frame, to which may also be connected a subject support (e.g., a bed) to place a subject in a position for scanning of the subject's patient bodily surface. In some embodiments, the optical sensor may be removable and/or hand-held. In some embodiments, the optical sensor includes a three-dimensional scanner. In some embodiments, the optical sensor includes an infrared detector. In some embodiments, the optical sensor is a laser scanner.

In some embodiments, the delivery system further includes: (c) a three-dimensional plotter operatively connected with the optical sensor; and (d) a controller operatively connected with the dispensing system.

In some embodiments, the dispensing system includes one or more cartridges loaded with a composition (e.g., a composition including cells, support compounds, growth factors, combinations thereof, etc.). In some embodiments, the cartridge includes and/or is in fluid communication with a plurality of printheads. In some embodiments, the printheads include nozzles configured for delivery of cells and/or compositions.

Methods of forming a tissue on a patient bodily surface of a patient in need thereof are also provided, including: (a) scanning the patient bodily surface to obtain the three dimensional coordinates thereof; and then (b) dispensing viable cells on the patient bodily surface of the patient based upon the coordinates to thereby form the tissue. In some embodiments, the dispensing step is performed two or more times in sequence to make a tissue having multiple layers.

Also provided are methods of processing patient bodily surface data obtained from a three dimensional optical detector to provide a path to a dispensing system operatively associated to the optical detector, the methods including: interpreting the patient bodily surface data from the optical detector to form a model of the patient bodily surface; transforming the model into a negative mold of the patient bodily surface, which mold is split into a plurality of Z-axis layers, which layers correspond to one or more tissue layers; and overlaying each of the tissue layers with a series of lines which cover the patient bodily surface, wherein the lines provide a path for the dispensing system. In some embodiments, the methods further include the step of obtaining the patient bodily surface data by scanning with a three-dimensional optical sensor. In some embodiments, the patient bodily surface data is wound surface data (e.g., skin wound surface data).

Further provided are systems for processing data of a patient bodily surface obtained from a three dimensional optical detector to provide a path to a dispensing system operatively associated to an optical detector, the system including: means for interpreting the patient bodily surface data from the optical detector to form a model of the patient bodily surface; means for transforming the model into a negative mold of the patient bodily surface, which mold is split into a plurality of Z-axis layers, which layers correspond to one or more tissue layers; and means for overlaying each of the tissue layers with a series of lines which cover the patient bodily surface, wherein the lines provide a path for the dispensing system. Some embodiments further include means for obtaining the patient bodily surface data. In some embodiments, the patient bodily surface data is wound surface data (e.g., skin wound surface data).

Computer program products are also provided for processing data of a patient bodily surface obtained from a three dimensional optical detector to provide a path to a dispensing system operatively associated to the optical detector, the computer program product including a computer readable medium having computer readable program code embodied therein, the computer readable program code including: computer readable program code which interprets the patient bodily surface data from the optical detector to form a model of the patient bodily surface; computer readable program code which transforms the model into a negative mold of the patient bodily surface, which mold is split into a plurality of Z-axis layers, which layers correspond to one or more tissue layers; and computer readable program code which overlays each of the tissue layers with a series of lines which cover the patient bodily surface, wherein the lines provide a path for the dispensing system. In some embodiments, the patient bodily surface data is wound surface data (e.g., skin wound surface data).

The foregoing and other objects and aspects of the present invention are explained in greater detail in the drawings herein and the specification set forth below.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 6 is an alternative embodiment of a delivery system (5) having an attached computer (40) and a cover (60) over the manipulator (20) and printhead support (10). The system (5) is attached to a table (30) having a bed (35).

FIG. 7 is a cutout view of a printer support (10) having a camera (11), infrared sensors (15), and a plurality of printer cartridges (14) attached thereto.

FIG. 8 is an exploded view of a printer cartridge (14).

DETAILED DESCRIPTION OF THE PREFERRED EMBODIMENTS

Figure 1:
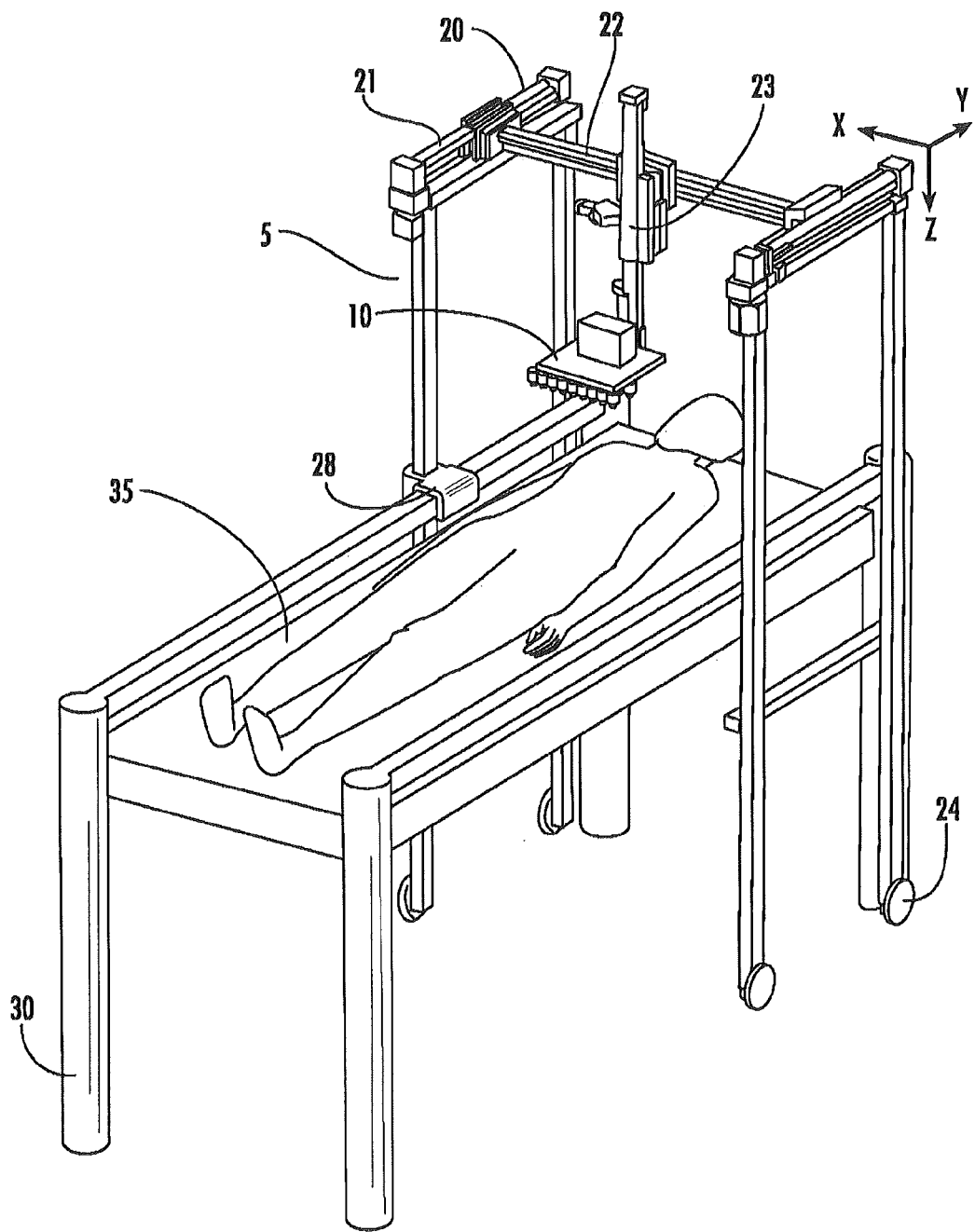
FIG. 1 is a perspective view of a delivery system (5) according to some embodiments of the present invention having a printhead support (10). This portable embodiment has wheels (24), and is positioned over a subject lying on a table (30) having a bed (35). The printhead support is operatively connected to a manipulator (20) having members (23, 22, 21) configured to allow the printhead support (10) to be moveable about the Z axis (member 23), the X axis (member 22), and the Y axis (member 21). A subject may lie on a table (30) having a bed (35). The system (5) may have one or more locks (28) to attach to the table (30).

Provided herein and further described below are systems, compositions, devices and methods useful for the delivery of cells and tissues onto a subject in need thereof. In some embodiments, a cartridge based cell delivery system including a dispensing system is provided, which dispensing system is operatively associated with an optical sensor.

Aspects of the present invention are described herein with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout. In the figures, the thickness of certain lines, layers, components, elements or features may be exaggerated for clarity.

The disclosures of all United States patent references cited herein are hereby incorporated by reference to the extent they are consistent with the disclosure set forth herein. As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" or "/" refers to and encompasses any and all possible combinations of one or more of the associated listed items, as well as the lack of combinations when interpreted in the alternative ("or").

Unless otherwise defined, all terms (including technical and scientific terms) used herein have the same meaning as commonly understood by one of ordinary skill in the relevant art. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The present invention is described herein, in part, with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

As illustrated in FIG. 1, in some embodiments a delivery system (5) is provided which includes a printhead support (10) thereon. In some embodiments, the delivery system may be provided on wheels (24) for portability. The delivery system (5) may be positioned over a subject lying on a table (30) having a bed (35) when in use. In some embodiments, a locking mechanism (28) may be provided to lock the delivery system (5) in place relative to the table (30) and/or bed (35). The printhead support (10) is operatively connected to a manipulator (20) having members (23, 22, 21) configured to allow the printhead support (10) to be moveable about the Z axis (member 23), the X axis (member 22), and the Y axis (member 21).

Figure 2:
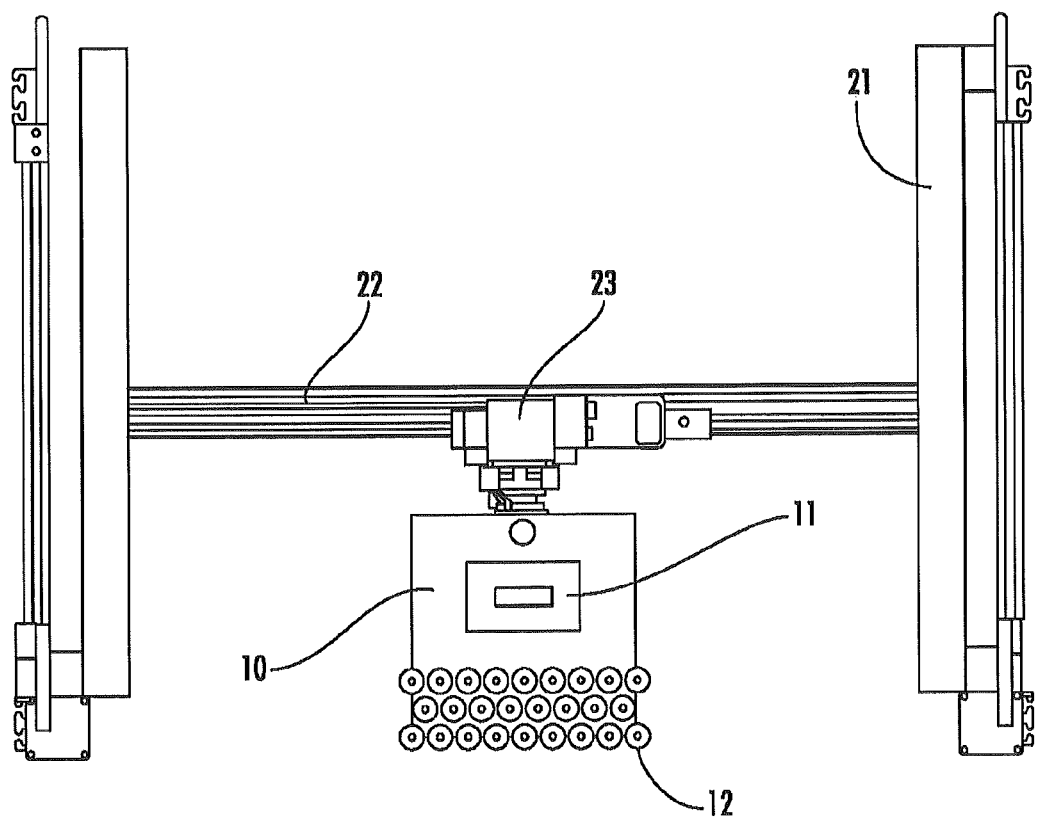
FIG. 2 is a bottom view of a printhead support (10) according to some embodiments having an optical sensor (11) and a plurality of printheads (12).

As illustrated in FIG. 2, in some embodiments the printhead support (10) includes an optical sensor (11) and a plurality of printheads (12). In other embodiments, the printhead support (10) includes a plurality of printheads (12), but the optical sensor (11) is provided on a separate support and/or can be (not shown).

Figure 3:
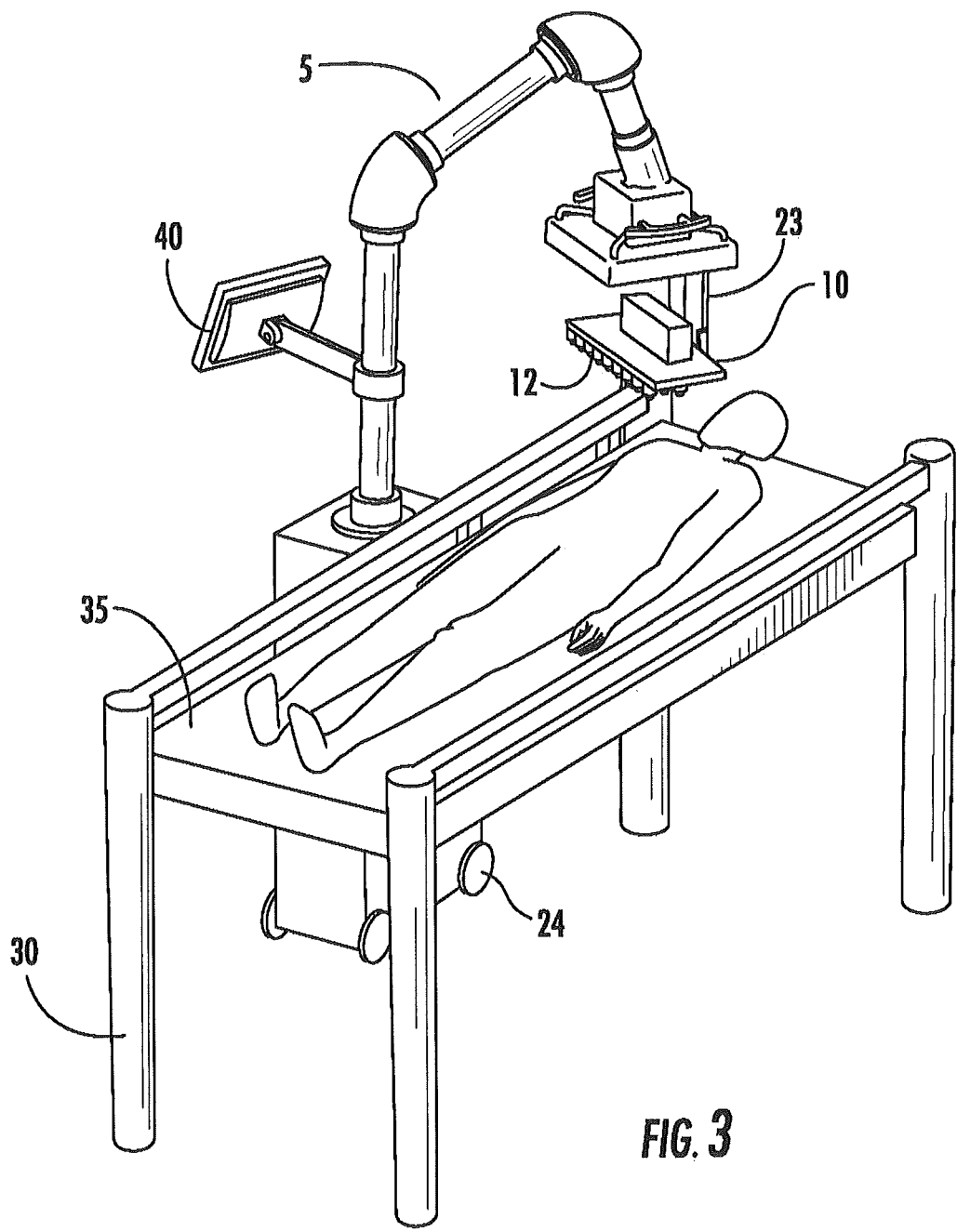
FIG. 3 is an alternative embodiment of a delivery system (5) having an attached computer (40), positioned over a subject lying on a table (30) having a bed (35). A cover (60) is provided above the printhead support (10) covering a portion (members 22 and 21, and the top of member 23) of the manipulator (20).
Figure 4:
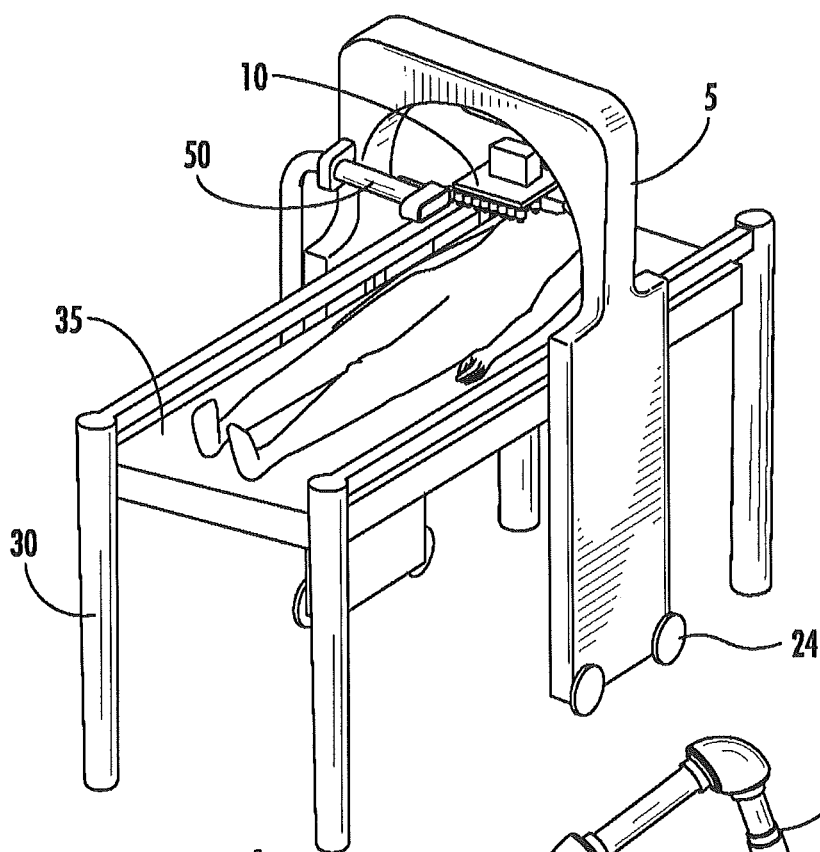
FIG. 4 is an alternative embodiment of a delivery system (5) having an attached light (50), positioned over a subject lying on a table (30).
Figure 5:
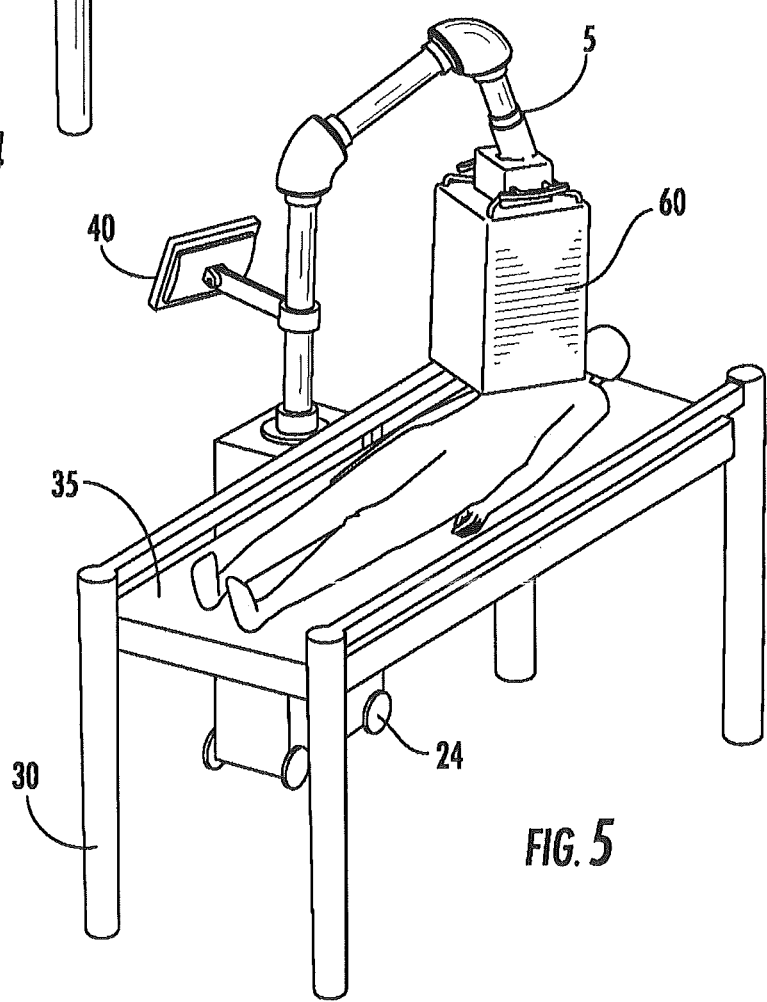
FIG. 5 is an alternative embodiment of a delivery system (5) having an attached computer (40) and a cover (60) covering the manipulator and the printhead support, positioned over a subject lying on a table (30).

Some alternative embodiments of the delivery system (5) are illustrated in FIGS. 3-6. FIG. 3 illustrates an embodiment of the delivery system having an attached computer (40), with the printer support (10) positioned over a subject lying on a table (30). FIG. 4 illustrates another embodiment, and includes an attached light (50), positioned over a subject lying on a table (30). FIG. 5 illustrates an embodiment having an attached computer (40) and a cover (60) over the printhead support (10), positioned over a subject lying on a table (30). FIG. 6 illustrates an embodiment of a delivery system (5) having an attached computer (40) and a cover (60) over the manipulator (20) and the printhead support (10). The delivery system (5) is attached to a table (30).

FIG. 7 illustrates an embodiment of a printhead support (10) having a camera (11), infrared sensors (15), and a plurality of cartridges (14). FIG. 8 provides an exploded view of one embodiment of a cartridge.

Figure 10:
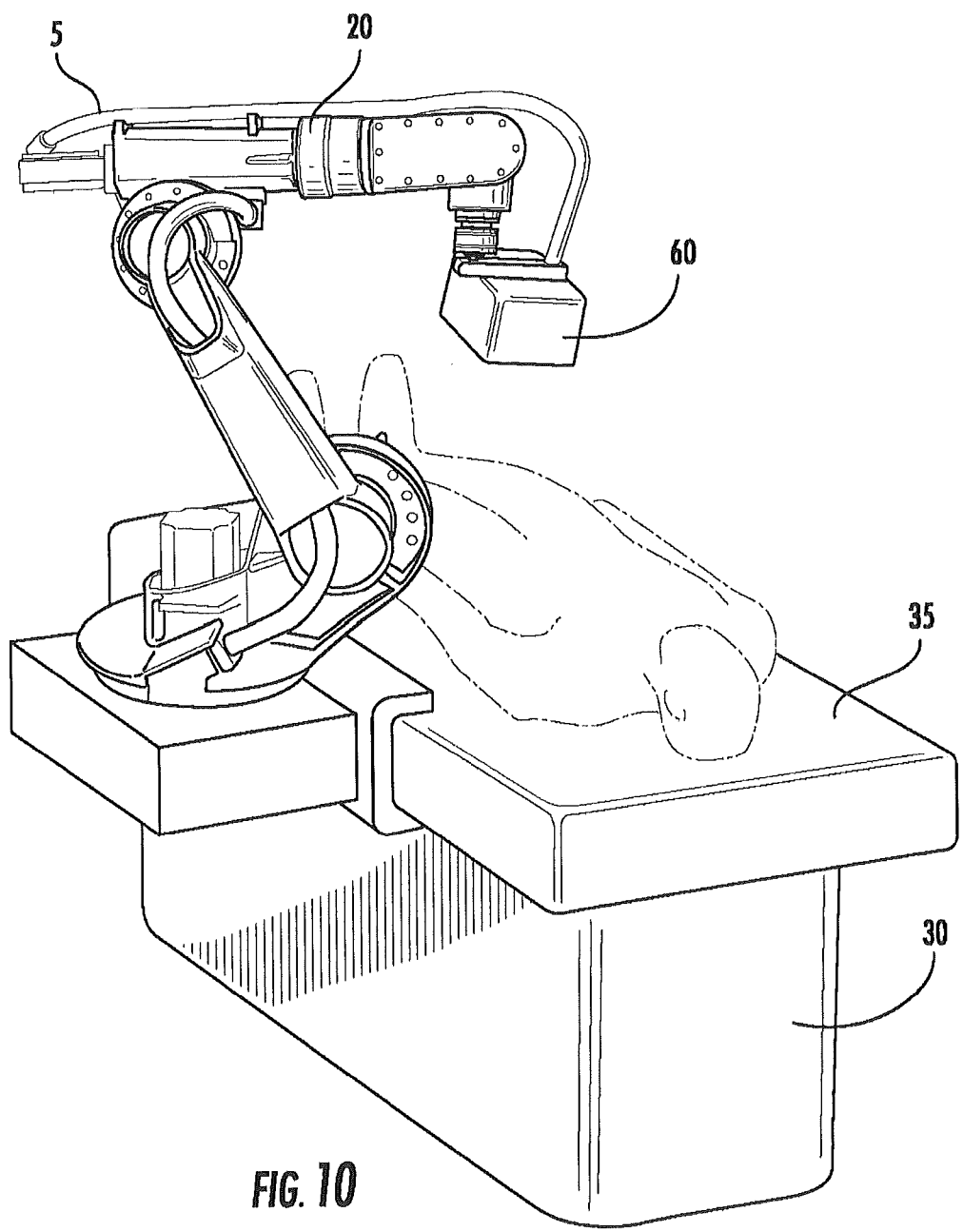
FIG. 10 is an alternative embodiment of a delivery system (5) having a robotic arm type manipulator (20) for movement about the XYZ axis, and having a cover (60) over the printhead support (not shown). The delivery system (5) is attached to a table (30) having a bed (35).

FIG. 10 illustrates an embodiment of a delivery system (5) having a robotic arm type manipulator (20) for movement about the XYZ axis, and having a cover (60) over the printhead support (not shown). The delivery system (5) is attached to a table (30) having a bed (35).

Figure 11:
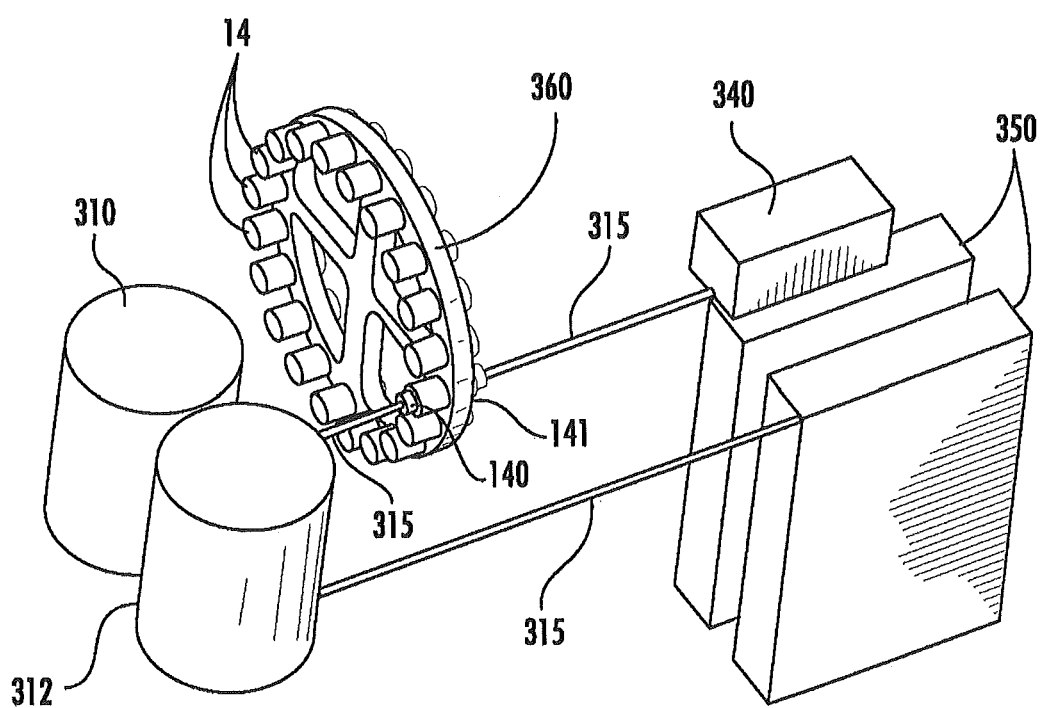
FIG. 11 is a representative embodiment of components of a dispensing system. Separate reservoirs are provided for carrier/support compositions (310) and crosslinker (312). Cartridges (14) containing cells and/or compositions are loaded into a motorized storage unit (360) that connects a cartridge (14) into fluid communication with the carrier/support composition. The cells and/or compositions are drawn into a mixing chamber (340) in which the cells and/or compositions can be mixed with the carrier/support compositions prior to dispensing to a target site. One or more pumps (350) are provided to draw carrier/support compositions and/or crosslinker into one or more printheads (not shown) for dispensing.

FIG. 11 illustrates an embodiment of components of a dispensing system. Separate reservoirs are provided for carrier/support compositions (310) and crosslinker (312). A storage unit (360), which may be motorized, is provided in which a plurality of cartridges (14) containing cells and/or compositions may be loaded. The cartridges (14) can be locked into fluid communication with the carrier/support composition according to some embodiments, using any appropriate locking mechanism known in the art. A first and second pump (350) are provided to draw carrier/support compositions and crosslinker, respectively, into one or more printheads (not shown) for dispensing. The cells and/or compositions in the cartridge (14) are drawn by the first pump (350) into a mixing chamber (340) in which the cells and/or compositions can be mixed with the carrier/support compositions held in the reservoir (310) prior to dispensing to the target site. In some embodiments, the cells and/or compositions may be connected in a manner to allow recirculating flow, e.g., to continually mix the cell solution with carrier (not shown).

Figure 12:
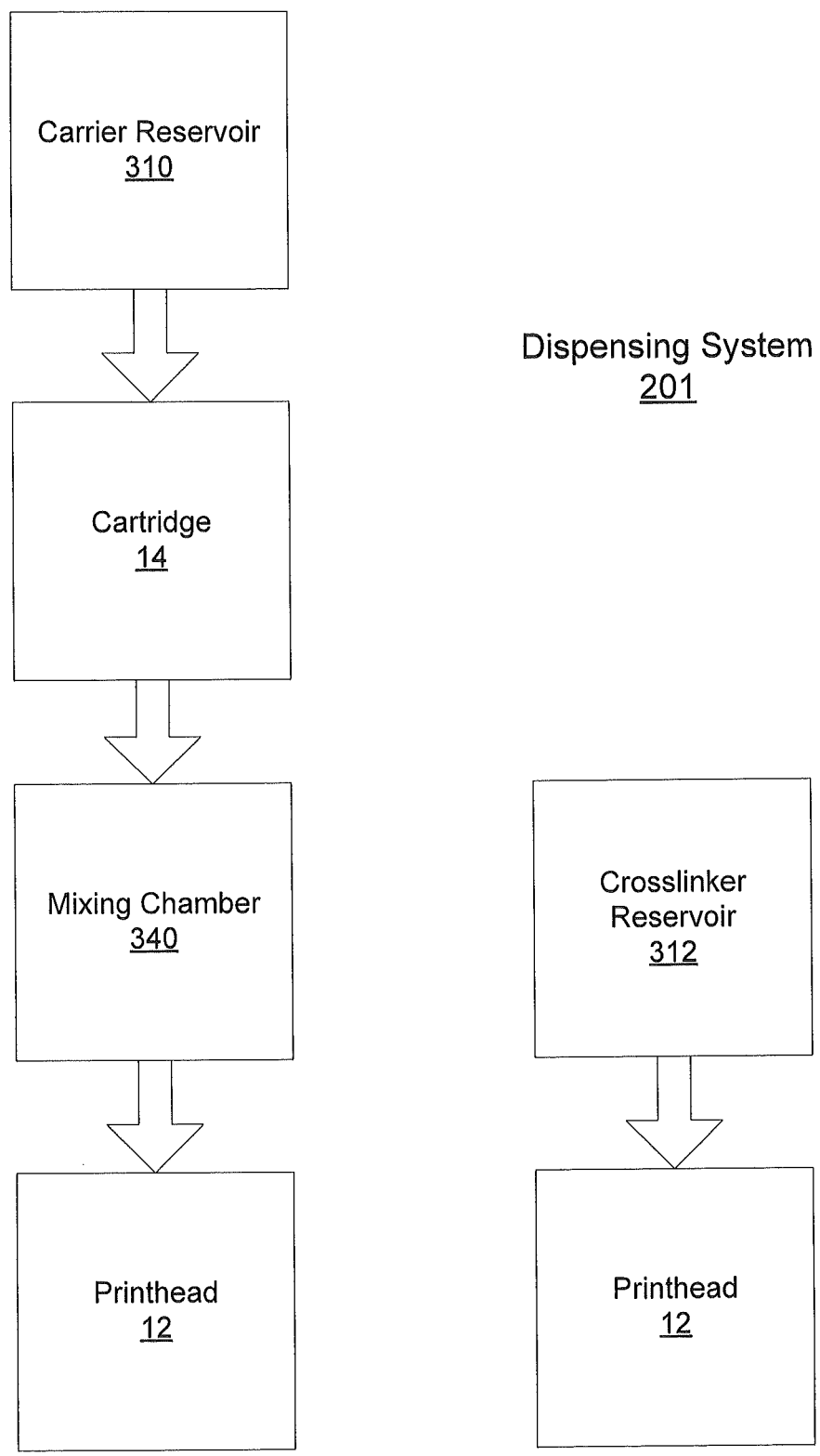
FIG. 12 is a schematic diagram of an embodiment of a dispensing system (201). The dispensing system includes a carrier reservoir (310) in fluid communication with a cartridge (14), which, in turn, is in fluid communication with a mixing chamber (340) in which the carrier and the cartridge contents can be mixed prior to delivery through a printhead (12). A separate crosslinker reservoir (312) is provided that is in fluid communication with a separate printhead (12), such that the crosslinker may be delivered contemporaneously with the mixed carrier and cartridge contents.

FIG. 12 provides a schematic diagram of an embodiment of a dispensing system (201) having a carrier reservoir (310) connected to a cartridge (14), which, in turn, is connected to a mixing chamber (340) in which the carrier and the cartridge contents can be mixed prior to delivery through a printhead (12). A separate crosslinker reservoir (312) is provided that may be connected to a separate printhead (12), such that the crosslinker may be delivered contemporaneously with the mixed carrier and cartridge contents. In some embodiments, a pump (not shown) may be provided to draw carrier and cartridge contents into the mixing chamber (340), where it is mixed. The mixed contents are then drawn into the printhead (12) and delivered to the target site.

Referring again to FIG. 11, in some embodiments, a cartridge (14) has at least one input port (140) and at least one output port (141). A separate reservoir (310) may have connectors (315) configured to fit into the input port (140) of a cartridge (14).

A locking mechanism may attach one or more of the connectors (315) to a cartridge (14) and aid in preventing the connections from breaking loose. In some embodiments, when moving to the next cartridge (14), the dispensing system releases the locked connections and spins the storage unit (360) to the next selected cartridge (14). Any suitable locking mechanisms known in the art may be used. For example, a threaded lock, pin-type lock, etc. See, e.g., U.S. Pat. No. 1,662,482 to Ward and U.S. Pat. No. 4,119,237 to Greenwald et al.

Each of the dispensing system components can be mounted anywhere on the system, depending on the size of the reservoirs (310 and 312) and storage unit (360). In some embodiments, one or more of the dispensing system components are mounted onto the manipulator (20). In some embodiments, larger components (e.g., reservoirs, pumps, storage unit) may be mounted to the frame, whereas smaller components (e.g., mixing chamber) may be mounted onto the manipulator (20).

An aspect of the present invention is the use of an apparatus as described herein in a method for generating tissue such as for treating a wound (e.g., burns, abrasions, lacerations, incisions, pressure sores, puncture wounds, penetration wounds, gunshot wounds, crushing injuries, etc.) in a subject in need thereof, in which cells and/or compositions are applied thereto in an amount effective to generate the tissue or treat the wound.

Accordingly, in some embodiments the apparatus may be used to dispense cells and/or compositions onto a patient bodily surface. "Bodily surface" as used herein refers to the exposed tissues of one or more body parts or a portion thereof (for example, skin or other tissues exposed upon injury thereof) which are detectable by the optical detector as described herein, and include, but are not limited to, that of the torso, chest, stomach, shoulder, back, buttocks, neck, head, face, cheek, lips, eyebrow, scalp, ear, chin, arm, elbow, hand, finger, leg, knee, foot, toe, etc. The surface may in some embodiments have a surface area of from 0.1, 0.5, 1, 5, 10, 20, or 50 $cm^2$, to 100, 120, 150, 200, 250, 500, 750 or 1000 $cm^2$.

Examples of wounds that can be treated with the present invention include burn wounds. Burn wounds are tissue injuries that can result from heat, chemicals, sunlight, electricity, radiation, etc. Burns caused by heat, or thermal burns, are the most common. Chemical burns resemble thermal burns. Though burn wounds tend to occur most often on the skin, other body structures may be affected. For example, a severe burn may penetrate down to the fat, muscle or bone. In some embodiments, cells corresponding to one or more of these tissues may be delivered onto the wound site, e.g., in a layer-by-layer application that mimics the natural tissues, as needed or desired.

Wounds may be characterized by the depth of injury as known in the art. For example, the degree of a burn is characterized as first, second or third depending on the depth of the tissues injured. In a first-degree burn, only the top layer of skin (the epidermis) is damaged. In second-degree burns, the middle layer of skin (the dermis) is damaged. Finally, in a third-degree burn, the most severe type, the damage is deep enough to affect the inner (fat) layer of the skin. Similarly, pressure sores of the skin are characterized as stage I (red, unbroken skin, erythema does not fade with release of pressure), stage II (disrupted epidermis, often with invasion into the dermis), stage III (injury of the dermis), and stage IV (subcutaneous tissue is exposed).

In pressure sore wounds, pressure-induced constriction of local capillaries results in ischemia in the affected skin. Similarly, a burn wound is ischemic due to associated capillary thrombosis. A diabetic ulcer is another example of a poorly perfused wound. For these types of wounds, where blood is not readily available to aid in the normal course of wound healing, in some embodiments dead and/or injured tissue is removed (debridement) prior to application of the cells and/or compositions as provided herein.

In some embodiments, compositions may include an antimicrobial agent to decrease the risk of infection. In some embodiments, compositions may include analgesics or anesthetics for pain relief, surfactants, anti-inflammatory agents, etc. See, e.g., U.S. Pat. No. 6,562,326 to Miller. Methods of attenuating swelling, such as treatment with cold (e.g., cool water, ice, etc.) and elevation of the affected area, may also be used.

According to some embodiments, the device may be used for both open wounds and closed wounds. In the case of closed wounds, the scanner and/or dispensing device may be allowed access to the wound site through surgical means, inclusive of endoscopic procedures.

In some embodiments, reapplication of the cells and/or compositions may be performed as needed. Cleansing to remove bacteria and debridement to remove necrotic debris may also be warranted during the course of treatment.

Application of a moisturizing cream or ointment may be used to soften wound eschar in order to assist in debridement.

A. Dispenser.

In some embodiments, cells, proteins, support materials, combinations thereof, etc., are delivered with a printer and/or other dispenser or dispensing system. "Dispenser" or "dispensing system" as used herein is a device that functions to deliver cells and/or compositions to a target site. In some embodiments, the cells and/or compositions in the dispensing system are delivered through a printhead or nozzle placed above a target site or in following a predetermined path across a target site.

"Printing" as used herein refers to the delivery of droplets of cells and/or compositions with small volumes, e.g., from 0.5 to 500 microLiters, or 5 to 100 microLiters, or from 10 to 75 microLiters per droplet. In some embodiments, droplets have a volume ranging from 0.5 to 500 picoLiters, or 5 to 100 picoLiters, or from 10 to 75 picoLiters per droplet. Printing may be performed by, e.g., using standard printers with print heads that are modified as described herein.

In some embodiments, printing can provide a precise delivery of cells and/or compositions to a resolution of approximately 5, 10, 20, 30, 40, 50, 60, 70, 80, 90, 100, or 200 μm. Printing can also deliver specific cells to specific target sites using a layer-by-layer fabrication. Such layer-by-layer fabrication may in some embodiments be performed in situ on a subject in need thereof, and involve multiple cell types arranged with precision. This is in contrast to cell seeding or spraying techniques, in which cells are randomly applied over a large area.

In some embodiments, cells and/or compositions are delivered to target sites using other dispensers such as a spray or stream. Such delivery allows continuous delivery of cells and/or compositions to a target site, which may serve to reduce the time needed for the application of the cells and/or compositions to the target site. See also U.S. Pat. No. 6,986,739 to Warren et al.

In some embodiments of stream dispensing, delivery pumps are activated when the printhead is over a target site and can deliver cells and/or compositions in lines of the same or varying widths across the site, as desired. For example, lines between 0.001 and 10 cm, or 0.01 and 1 cm, or 0.1 and 0.5 cm may be provided according to some embodiments.

In some embodiments, the dispenser may include both a printer and another dispensing system such as a spray or stream. In such a system, the spray or stream may be used for faster but less precise delivery, while the printer may be used for slower but more precise delivery of cells and/or compositions to the target site.

As used herein, the "printhead" is the portion of a printer or other dispensing device that applies droplets, sprays or streams of cells and/or compositions onto the target site. In some embodiments, the printhead includes one or more nozzles attached thereto, through which the cells and/or compositions are passed from the dispensing system to a target site.

A "cartridge" as used herein refers to a vessel or reservoir in which cells and/or compositions may be held, and which is in fluid communication with one or more nozzles and/or one or more printheads. The cartridge may include the reservoir and printhead in a single unit, as in a traditional inkjet cartridge, or the reservoir and nozzle may be in separate units but connected such that they are in fluid communication (e.g., through the use of a connector such as tubing). In some embodiments, cartridges may hold from 0.5 mL to 25 mL, or from 1 mL to 15 mL, or from 5 mL to 10 mL in volume.

In some embodiments, one or more cell types and/or compositions are loaded into an individual cartridge. "Compositions" may include cells, carriers (e.g., hydrogels), support materials, crosslinkers, macromolecules such as proteins, cytokines, growth factors, etc., or any combination thereof. Compositions may also include oxygen generating biomaterials. See, e.g., PCT Publication WO 2008/124126.

In some embodiments, the compositions may be provided in a larger container (e.g., reservoir) than that cartridge. In some embodiments, the container may hold from 5 mL to 5 L, or from 10 mL to 1 L, or from 15 mL to 500 mL in volume of the composition (e.g., carrier, support materials, crosslinkers, etc.).

In some embodiments, each cartridge may be configured to connect to multiple nozzles and/or printheads, in contrast to standard inkjet printing in which one printhead is connected to one cartridge. This allows arbitrary printhead configurations that can conform to the needs of the treatment. It also increases the throughput of the system and provides a rapid method of sterilization by attaching a cartridge of cleaning fluid to the printheads.

In some embodiments, the printheads contain pressure-based nozzles. A pressure-based delivery system according to some embodiments allows the printer or other dispenser to remain a safe distance above the patient and to accommodate a variety of body types. As used herein, a "pressure-based" delivery system uses three components: the pressure source, material reservoirs, and delivery mechanism.

In some embodiments, the delivery mechanism is a series of voltage operated inkjet valves. The pressure source is operatively connected to the reservoir, which is in fluid communication with the delivery mechanism. In some embodiments, a gas (e.g., air, air plus 5% $CO_2$, etc.) is pumped into empty space in the reservoir by the pressure source, which in turn drives the material in the reservoir (cells and/or compositions) into the delivery mechanism.

In some embodiments, the printhead is equipped with a DC solenoid inkjet valve. In some embodiments, one or more, or several, reservoirs for loading cells are connected to the inkjet valve. In some embodiments, the cells and/or compositions may be supplied from the reservoirs to the valve or nozzle by air pressure.

In some embodiments, the dispenser includes a two-dimensional (X-Y) or three-dimensional (X-Y-Z) plotter (e.g., driven by step motors). In some embodiments, the printhead may be mounted on an X-Y-Z plotter to allow precise deposition of cells onto a target site. Positioning of the XYZ plotter under the printhead may be controlled via a controller. In some embodiments, the controller acquires the positioning information from software loaded on a computer. In some embodiments, the software converts the image of the target to a four-byte protocol, which is used to activate specific inkjet valves and coordinate the X-Y-Z position.

A pressure-based system may be preferable in some embodiments as compared to inkjet cartridges in the context of in situ printing because it separates the reservoir and delivery mechanism. A traditional inkjet cartridge includes the reservoir and delivery mechanism in a single unit. If either the reservoir or delivery mechanism fails, then the entire unit fails. Furthermore, inkjet cartridges must be filled and sealed prior to printing. If the inkjet cartridge is filled with cells, failure of the cartridge means the loss of all cells contained in that cartridge. Embodiments of the delivery systems described herein solve both of these issues. The reservoir and delivery mechanism can be replaced individually in the case of failure of either component. Material is only pumped to the delivery mechanism when it is needed, so failure of the delivery mechanism should not result in the loss of all material in the reservoir.

In addition, in some embodiments the pressure-based system can provide a method of detecting and clearing clogged valves. By placing a pressure sensor at the end of the valve, the delivery pressure can be compared to the applied pressure. If the difference between the two pressures is larger than a certain threshold, then the valve is clogged. Redirecting the output of the valve to a waste reservoir and applying a large burst of pressure may be used to try and clear the valve. If the clearing process fails, then the delivery system will detect this and can continue printing without using that valve.

In some embodiments, the dispenser is driven by a pressure provided by internal pumps. In some embodiments, the pumps draw cells and/or compositions from one or more cartridges into a chamber. The chamber may be configured to allow mixing of cells and/or compositions held in separate cartridges prior to dispensing to the target site. In some embodiments, there is a pump operatively associated with the printhead that draws the mixed material into the printhead for dispensing.

In some embodiments, pumps may be provided to draw compositions through the dispensing system or a portion thereof through negative pressure and/or positive pressure. In some embodiments, the pump is a variable speed pump designed to have a flow rate in the dispenser between 0.01 mL/second and 1 mL/sec or between 0.03 mL/sec and 0.07 mL/sec; a flow rate between 0.1 mL/sec and 1 mL/sec or between 0.25 mL/sec and 0.65 mL/sec; and/or a flow rate between 0.5 mL/sec and 0.45 mL/sec. In some embodiments, the pump has a variable flow rate inclusive of rates about 0.05 mL/second; about 0.45 mL/sec; and/or about 0.25 mL/sec (e.g., no more than 10, 15 or 20% above or below these values).

In some embodiments, a system of pumps draws gel out of the reservoir, through the cartridge, into the mixing chamber, and then into the printhead. In some embodiments, this system is closed and does not require an outside pressure source to move material into the printhead. In some embodiments, a continuous line is provided, and pumps are configured to supply negative and/or positive pressure to move cells and/or compositions through the line without the need for an open pressure source such as compressed gas, thus providing a closed system in which the cells can be maintained in a sterile environment.

In some embodiments, at least a portion of the dispenser components are housed in a container configured to maintain a temperature of about 37 degrees Celsius. In some embodiments, at least a portion of the dispenser components are kept at room temperature. In some embodiments, at least a portion of the dispenser components are kept at a temperature lower than room temperature (e.g., about 4 degrees Celsius). In some embodiments, at least a portion of the dispenser are housed in a container configured to vary the temperature as desired (e.g., from about 4 degrees Celsius to room temperature, from room temperature to about 37 degrees Celsius, or from about 4 degrees Celsius to about 37 degrees Celsius).

Cells may be printed in the form of a composition that contains a carrier. The cells may be provided in the form of a suspension, solution, or any suitable form. The carrier may be a solid or a liquid, or both (e.g., a gel). In some embodiments, the cells are provided as a suspension in the carrier to reduce clumping of the cells. Support compounds, growth factors, etc., may be included in compositions having cells and/or may be included in compositions without cells (but may include a suitable carrier), as desired.

Suitable gels include, but are not limited to, agars, collagen, fibrin, hyaluronic acid, including hydrogels thereof, etc, Besides gels, other support compounds may also be utilized in the present invention, Extracellular matrix analogs, for example, may be combined with support gels to optimize or functionalize the gel. One or more growth factors may also be included. In some embodiments a temperative sensitive gel may be used, Examples of temperature sensitive gels include thermaosensitive hydrogels and thermosensitive polymer gels (e.g., a poloxamer such as Pluronic® F-127 (BASF corporation, Mont Olive, N.J.)). See also U.S. Pat. Nos. 6,201,065, 6,482,435.

Other examples of suitable liquid carriers include, but are not limited to, water, ionic buffer solutions (e.g., phosphate buffer solution, citrate buffer solution, etc.), liquid media (e.g., modified Eagle's medium ("MEM"), Hanks' Balanced Salts, etc.), and so forth. The use of a liquid or gel carrier in the cell composition may in some embodiments promote adequate hydration and minimize evaporation of the cells after printing.

In some embodiments, cells may also be transfected (e.g., with a specific gene) with material of interest. Useful genetic material may be, for example, genetic sequences that are capable of reducing or eliminating an immune response in the host. For example, the expression of cell surface antigens such as class I and class II histocompatibility antigens can be suppressed. This would allow the transplanted cells to have a reduced chance of rejection by the host. Cells may also be transfected with a gene encoding one or more growth factors. According to some embodiments, cells may be transfected during the printing process. See PCT publication WO 2008/153968 to Xu et al.

The present invention includes the building of tissues by the appropriate combination of cell and support material, or two or three or more different cell types typically found in a common tissue, preferably along with appropriate support compound or compounds, and optionally with one or more appropriate growth factors. Cells, support compounds, and growth factors may be dispensed from separate nozzles or through the same nozzle in a common composition, depending upon the particular tissue (or tissue substitute) being formed. Dispensing may be simultaneous, sequential, or any combination thereof. Some of the ingredients may be dispensed in the form of a first pattern (e.g., an erodable or degradable support material), and some of the ingredients may be dispensed in the form of a second pattern (e.g., cells in a pattern different from the support, or two different cell types in a different pattern). Again, the particular combination and manner of dispensing will depend upon the particular tissue construct desired.

In embodiments in which increased delivery precision is desired, the dispenser includes a printer having thermal or piezoelectric printheads and/or inkjet cartridges for increased delivery precision. Methods and compositions for the inkjet printing of viable cells are known and described in, for example, U.S. Pat. No. 7,051,654 to Boland et al.; Wilson et al. (2003) The Anatomical Record Part A 272A: 491-496.

In some embodiments, cells/compositions are dispensed by printing with a modified inkjet printer. Modifications may include, but are not limited to, means to control the temperature, humidity, shear force, speed of printing, and firing frequency, by modifications of, e.g., the printer driver software and/or the physical makeup of the printer. See, e.g., Pardo et al, (2003) *Langmuir* 19:1462-1466; U.S. Pat. No. 7,051,654 to Boland et al. Not every modification suggested in these references will be suitable to a given application, as will be appreciated by those skilled in the art. For example, in some embodiments, printers are not modified by using new gear mount pillars with closer tolerances by adding a horizontal support, changing the transistor in the circuit to one with higher amplification, and reentering the horizontal position encoder. Also, in some embodiments, printer software is not modified to lower the resistive voltages to avoid heating of the solutions above 37° C.

In some embodiments, printers (e.g., the commercial printers HP695C and HP550C) may be modified as follows. The printer top cover may be removed and the sensor for the cover disabled. The paper feeding mechanism may be disabled to allow printing of cells onto solid substrates (e.g., scaffolds). The ink absorbing pads (which are on the right side of the HP695C and HP550C printers) may be removed (e.g., to avoid the pads contaminating the bottom of the print cartridges during the printing process). To offer the capability of the printer to print 3D constructs, a customized Z-axis module with a controlled elevator chamber may be added.

In some embodiments, the printer is a thermal bubble inkjet printer. In general, in a thermal bubble inkjet printer, resistors create heat in the print head, which vaporizes ink to create a bubble. As the bubble expands, some of the ink is pushed out of a nozzle onto the paper. A vacuum is created when the bubble collapses, which pulls more ink into the print head from the cartridge. In the present invention, the ink is replaced with, e.g., cells and/or compositions of interest (e.g., cells in a liquid carrier), and the paper is replaced with a suitable substrate, e.g., an agar or collagen coated substrate, or a suitable scaffold. See, e.g., U.S. Pat. No. 6,537,567 to Niklasen et al.

In other embodiments, cells are printed using a piezoelectric crystal vibration print head. In general, a piezoelectric crystal receives an electric charge that causes it to vibrate, forcing ink out of the nozzle, and pulling more ink into the reservoir. In the present invention, the ink is replaced with, e.g., cells and/or compositions of interest. Compared with the thermal inkjet printing, the piezo-based inkjet printing usually requires more power and higher vibration frequencies. Typical commercial piezo-printers use frequencies up to 30 kHz and power sources ranging from 12 to 100 Watts. Therefore, in some embodiments a piezoelectric crystal vibration print head is used, with a vibrating frequency of 1, 5, 10 or 15, to 20, 25, 30, or 35 or more kHz, and power sources from 5, 10, 20, 50, 100, 120, or 150, to 200, 250, 300, 350, or 375 or more Watts.

In some embodiments, the printhead nozzles are each independently between 0.05 and 200 μm in diameter, or between 0.5 and 100 μM in diameter, or between 10 and 70 μm, or between 20 and 60 μm in diameter. In further embodiments, the nozzles are each independently about 40 or 50 μm in diameter. In still further embodiments, the nozzles are each independently between 0.1 or 0.5 and 2 or 3 mm. A plurality of nozzles with the same or different diameters may be provided. A more narrow nozzle may give greater precision delivery but low throughput, and vice versa. These may be provided according to cell type and/or precision desired. Though in some embodiments the nozzles have a circular opening, other suitable shapes may be used, e.g., oval, square, rectangle, etc., without departing from the spirit of the invention.

In some embodiments, the printhead nozzles and/or dispensing system is configured to deliver compositions as drops. In some embodiments, the drops may be 0.5, 1, 10 or 50 microliters, to 75, 100, 150, 200, 250, 300, 350, 400, 450, or 500 microliters in volume.

In some embodiments, the dispensing system is configures to deliver a layer of cells/compositions at a rate of 1, 5, 7, 10, 15, 20, 25, or 30 minutes, to 45, 60, 90, or 120 minutes per cell layer.

In some embodiments, the cells/compositions are formulated to provide an encapsulated form upon dispensing. The encapsulation of cells in permeable capsules is known and described in, for example, U.S. Pat. No. 6,783,964. For example, the cells may be encapsulated in a microcapsule of from 50 or 100 μm to 1 or 2 mm in diameter that includes an internal cell-containing core of polysaccharide gum surrounded by a semipermeable membrane; a microcapsule that includes alginate in combination with polylysine, polyornithine, and combinations thereof. Other suitable encapsulating materials include, but are not limited to, those described in U.S. Pat. No. 5,702,444.

"Encapsulated" cells are cells or small clusters of cells or tissue that are surrounded by a selective membrane laminate that allows passage of oxygen and other required metabolites, releases certain cell secretions (e.g., insulin), but limits the transport of the larger agents of the host's immune system to prevent immune rejection. Encapsulation may be useful for, e.g., the delivery of cells and/or tissues containing xenogeneic or allogeneic cells while reducing the risk of immune rejection in a host. This may be useful, e.g., to treat diseases due to inadequate or loss or secretory cell function, or ailments that would benefit from the addition of certain secretory cells. "Microencapsulation" of cells is where one, two, three or several cells are encapsulated. In some embodiments, each membrane encapsulates 10 cells or less, preferably 5 cells or less, of at least 50, 70, 80, 90 or 95% or more of the printed cells. See also U.S. Patent Application Publication No. 2009/0208577 to Xu et al.

In some embodiments, two or more layers may be separately applied, with subsequent layers applied to the top surface of previous layers. The layers can, in one embodiment, fuse or otherwise combine following application or, alternatively, remain substantially separate and divided following application to the subject.

The thickness of a printed layer (e.g., cell layer, support layer, etc.) may generally vary depending on the desired application. For example, in some embodiments, the thickness of a layer containing cells is from about 2 micrometers to about 3 millimeters, and in some embodiments, from about 20 micrometers to about 100 micrometers. Further, as indicated above, support compounds, such as gels, may be used to facilitate the survival of printed cells.

"Support compounds" which may be included in compositions may be any naturally occurring or synthetic support compound, including combinations thereof, suitable for the particular tissue being printed. In general, the support compound is preferably physiologically acceptable or biocompatible. Suitable examples include, but are not limited to, alginate, collagen (including collagen VI), elastin, keratin, fibronectin, proteoglycans, glycoproteins, polylactide, polyethylene glycol, polycaprolactone, polycolide, polydioxanone, polyacrylates, polysulfones, peptide sequences, proteins and derivatives, oligopeptides, gelatin, elastin, fibrin or fibrinogen, laminin, polymethacrylates, polyacetates, polyesters, polyamides, polycarbonates, polyanhydrides, polyamino acids carbohydrates, polysaccharides and modified polysaccharides, and derivatives and copolymers thereof (see, e.g., U.S. Pat. Nos. 6,991,652 and 6,969,480) as well as inorganic materials such as glass such as bioactive glass, ceramic, silica, alumina, calcite, hydroxyapatite, calcium phosphate, bone, and combinations of all of the foregoing. The support compound may be provided in a hydrogel, and crosslinked after delivery, if desired.

When dispensing certain types of two-dimensional or three-dimensional tissues or portions thereof, it is sometimes desired that any subsequent cell growth is substantially limited to a predefined region. Thus, to inhibit cell growth outside of this predefined region, compounds may be printed or otherwise applied to the print area that inhibit cell growth and thus form a boundary for the printed pattern. Some examples of suitable compounds for this purpose include, but are not limited to, agarose, poly(isopropyl N-polyacrylamide) gels, and so forth.

In one embodiment, for instance, this "boundary technique" may be employed to form a multi-layered, three-dimensional tube of cells, such as blood vessels. For example, a cell suspension may be mixed with a first gel ("Gel A") in one nozzle, while a second gel ("Gel B") is loaded into another nozzle, Gel A induces cell attachment and growth, while Gel B inhibits cell growth. To form a tube, Gel A and the cell suspension are printed in a circular pattern with a diameter and width corresponding to the diameter and wall thickness of the tube, e.g., from about 3 to about 10 millimeters in diameter and from about 0.5 to about 3 millimeters in wall thickness. The inner and outer patterns are lined by Gel B defining the borders of the cell growth. For example, a syringe containing Gel A and "CHO" cells and a syringe containing Gel B may be connected to the nozzle. Gel B is printed first and allowed to cool for about 1 to 5 minutes. Gel A and CHO cells are then printed on the agarose substrate. This process may be repeated for each layer.

B. Optical Detector.

In some embodiments, the area or areas of interest onto which cells and/or compositions are to be delivered is detected by an optical detector device to determine the two-dimensional and/or three-dimensional map thereof. The optical detector is, in some embodiments, operatively associated with an attached cell delivery device, such that the cell delivery pattern may be optimized for in situ delivery of the cells and/or compositions based upon such map.

"Map" as used herein refers to the two- and/or three-dimensional surface measurements, coordinates, and/or any other data that may represent the two- and/or three-dimensional surface of an area of interest (e.g., a wound). The map may be updated by scanning at any time, and/or in real time during delivery of cells and/or compositions.

As used herein, the "optical detector" may comprise one or more detectors that detect light at various wavelengths, e.g., visible light, infrared, ultraviolet, combinations thereof, etc. In some embodiments, both visible light and infrared light are detected. The optical detector may also have a depth detector to allow portability and/or account for movement of a subject during the scanning.

In some embodiments, optical reference points (e.g., dots, lines, etc.) may be placed around the wound area or in proximity thereof, which may be used to calibrate the optical detector. This may allow the subject to be moved without the need to re-calibrate the optical detector.

In some embodiments, an optical detector such as a camera may be used to capture images that coincide with the surface measurements of the area of interest. In some embodiments, an image sensor is used to collect light reflected from an object and generate an image of the object. A mirror and lens system may be combined with the imaging device to focus the light reflected by the object onto the image sensor. The image sensor may be one of a charge coupled device (CCD) and a complementary metal oxide semiconductor (CMOS), typically arranged into an area array, although the invention is not so limited. The number of sensors, each representing a pixel (short for "picture element"), determine the resolution of the image taken. A pixel is the smallest unit that makes up a digital image, and can represent the shade and/or color of a portion of an image. The output of a set of image sensors may be encoded as a set of pixels to create a digital image. The digital image may be stored in a compressed format such as in a jpeg, tiff, and/or gif format, among others. The image may then be stored in a digital storage device and may be displayed on a monitor by a display application.

In some embodiments, the optical detector is a three dimensional scanner such as that described in U.S. Pat. No. 6,856,407 to Knighton et al. (incorporated by reference herein), in which depth data for a three-dimensional object may be calculated from an intensity difference resulting from an intensity gradient projected on the object capturing an intensity at a location on a surface in a single pixel of an image sensing array (ISA). The intensity may be converted into a measurement of distance to the location relative to a reference point independently of data from other pixels of the ISA and independent of time of flight of light reflected from the location to the single pixel. A plurality of captures of the intensity at the location may be compared under different conditions to compensate for non-homogeneous environments or surfaces.

In some embodiments, the optical detector is a three dimensional scanner as described in U.S. Patent Application Publication No. 2005/0237581 to Knighton et al. (incorporated by reference herein). The scanning device may be used to generate three dimensional representation of an area of interest. As used herein, three dimensional representations may be any type of digital modeling, abstraction and/or similar techniques that may utilize depth maps, polygon meshes, parametric solids, point clouds and similar data structures to create and store a three dimensional representation of the scanned object. The scanner may include a lens or set of lenses to focus light on one or more image sensing arrays (ISA). In some embodiments, the ISAs may be a charged coupled device (CCD), complementary metal oxide semiconductor (CMOS) sensor, or similar imaging array. In some embodiments, lenses may be replaced by and/or supplemented with a reflector, light guide and/or similar article. By varying the focal settings, different aspects of the relief of an object may be brought into focus on an ISA. In some embodiments, an optical system having one or more optical elements distributes a same view of a target to a plurality of ISA's, each having a different focal range relative to the target.

Stereovision may also be used. Traditional stereovision methods estimate shape by establishing spatial correspondence of pixels in a pair of stereo images. A new concept called spacetime stereo has been developed, which extends the matching of stereo images into the time domain. By using both spatial and temporal appearance variations, it was shown that matching ambiguity could be reduced and accuracy could be increased. The shortcoming of spacetime stereo or any other stereo vision method is that matching of stereo images is time-consuming, therefore making it difficult to reconstruct high-resolution 3D shapes from stereo images in real time.

Further vision based surface mapping techniques may use structured light, which includes various coding methods and employs varying number of coded patterns. Unlike stereo vision methods, structured light methods usually use processing algorithms that are much simpler. Therefore, it becomes possible to achieve real-time performance, i.e., measurement and reconstruction. For real-time shape measurement, there are basically two approaches. The first approach is to use a single pattern, typically a color pattern. The use of this approach employs a color-encoded Moire technique for high-speed 3D surface contour retrieval. Other techniques use a rainbow 3D camera for high-speed 3D vision. Still others use a color structured light technique for high-speed scans of moving objects. Because these methods use color to code the patterns, the shape measurement result is affected to varying degrees by the variations of the object surface color. In general, better accuracy is obtained by using more patterns.

Another structured light approach for real-time shape measurement is the use of multiple coded patterns with rapid switching between them so that they could be captured in a short period of time. This approach has been used and develops a real-time 3D model measurement system that uses four patterns coded with stripe boundary codes. Some embodiments may provide an acquisition speed of about 15 fps, which is sufficient for scanning slowly moving objects. However, like any other binary-coding method, the spatial resolution of these methods is relatively low because the stripe width must be larger than one pixel. Moreover, switching the patterns by repeatedly loading patterns to the projector may limit the switching speed of the patterns and therefore the speed of shape measurement.

Another example of an optical detector is found in U.S. Pat. Nos. 6,788,210 and 6,438,272 (incorporated by reference herein), which provide a vision system for real-time and high-speed 3D shape measurement, with full capability of providing fast updating of the 3D surface maps and maps of the curves indicating the treatment areas and positioning markings such as tick marks of the said curves. In this manner, the sensor may serve to close the present automated debridement system control loop and as the means to provide for safe operation of the system, by for example, shutting the treatment laser beam off when the error between the actual position and desired position of the treatment laser beam is more than a selected (programmed) threshold. This method is based on a rapid phase-shifting technique. This technique uses three phase-shifted, sinusoidal grayscale fringe patterns to provide pixel-level resolution. The patterns are projected to the object with a switching speed of 240 fps. This system takes full advantage of the single-chip DLP technology for rapid switching of three coded fringe patterns. A color fringe pattern with its red, green, and blue channels coded with three different patterns is created by a PC. When this pattern is sent to a single-chip DLP projector, the projector projects the three color channels in sequence repeatedly and rapidly. To eliminate the effect of color, color filters on the color wheel of the projector are removed. As a result, the projected fringe patterns are all in grayscale. A properly synchronized high-speed B/W CCD camera is used to capture the images of each color channel from which 3D information of the object surface is retrieved. A color CCD camera, which is synchronized with the projector and aligned with the B/W camera, is also used to take 2D color pictures of the object at a frame rate of 26.7 fps for texture mapping. Together with the fast 3D reconstruction algorithm and parallel processing software, high-resolution, real-time 3D shape measurement is realized at a frame rate of up to 40 fps and a resolution of 532×500 points per frame. Other systems for 3D shape measurement known in the art can also be used in the system and methods of the present invention, such as those commercially available from Blue Hill Optical Technologies, located in Norwood, Mass. or Nutfield Technology, Windham, N.H.

For the projection of the computer-generated patterns, a single-chip DLP projector is used, which produces images based on a digital light switching technique. With this system, a complex facial surface has been mapped at 40 fps (the accuracy of the system being 0.1×0.1×0.1 mm), providing an excellent speed and resolution for the present automated laser debridement and treatment systems and the like.

The color image is produced by projecting the red, green, and blue channels sequentially and repeatedly at a high speed. The three color channels are then integrated into a full color image. To take advantage of this projection mechanism of a single-chip DLP projector, a color pattern which is a combination of three patterns in the red, green, and blue channels is created. The projector has no color filters for a monochrome mode of operation. As a result, when the color pattern is sent to the projector, it is projected as three grayscale patterns, switching rapidly from channel to channel at 240 fps. A high-speed B/W camera, which is synchronized with the projector, is used to capture the three patterns rapidly for real-time 3D shape measurement. An additional color camera is used to capture images for texture mapping. To obtain 3D maps and color information simultaneously, multi-threading programming is used to guarantee that two cameras work independently and that the timing of image grabbing is only determined by the external trigger signal.

For more realistic rendering of the object surface, a color texture mapping method may be used that is based on a sinusoidal phase-shifting method. In this method, the three fringe patterns have a phase shift of $2\pi/3$ between neighboring patterns. Since averaging the three fringe patterns washes out the fringes, a color image can be obtained without fringes by setting the exposure time of the color camera to one projection cycle or 12.5 ms.

These systems provide the capability of rapidly projecting and capturing three coded patterns rapidly. The employed fast three-step phase-shifting method provides a real-time 3D reconstruction speed and high measurement accuracy of the order of 0.1×0.1×0.1 mm. The sinusoidal phase-shifting method that has been used extensively in optical metrology to measure 3D shapes of objects at various scales. In this method, a series of phase-shifted sinusoidal fringe patterns are recorded, from which the phase information at every pixel is obtained. This phase information helps determine the correspondence between the image field and the projection field. Once this correspondence is determined, the 3D coordinate information of the object can be retrieved based on triangulation. A number of different sinusoidal phase-shifting algorithms are available. A three-step phase-shifting algorithm similar to the traditional three-step algorithm may be used, which requires three phase-shifted images.

In some embodiments, the optical detector accounts for movement of the subject (e.g., breathing movements of the torso) by including a range camera that interprets 3D scene information from a continuously-projected infrared structured light. In some embodiments, the optical detector includes an RGB camera and depth sensor. The depth sensor may include an infrared laser projector combined with a monochrome CMOS sensor, which captures video data in 3D under ambient light conditions. The sensing range of the depth sensor may be adjustable, and in some embodiments the device software is capable of automatically calibrating the sensor based on the detected environment, accommodating for a variety of targets and body types.

C. Cells and Tissues.

Any type of cell may be printed using the methods herein, including, but not limited to, mammalian cells (including mouse, rat, dog, cat, monkey and human cells), including somatic cells, stem cells, progenitor cells and differentiated cells, without limitation. Stem cells have the ability to replicate through numerous population doublings (e.g., at least 60-80), in some cases essentially indefinitely, and also have the ability to differentiate into multiple cell types (e.g., is pluripotent or multipotent). It is also possible for cells to be transfected with a compound of interest that results in the cells becoming immortalized (i.e., able to double more than 50 times). For example, it has been reported that mammalian cell transfection with telomerase reverse transcriptase (hTERT) can immortalize neural progenitor cells (See U.S. Pat. No. 7,150,989 to Goldman et al.).

"Embryonic stem cell" as used herein refers to a cell that is derived from the inner cell mass of a blastocyst and that is pluripotent.

"Amniotic fluid stem cell" as used herein refers to a cell, or progeny of a cell, that (a) is found in, or is collected from, mammalian amniotic fluid, mammalian chorionic villus, and/or mammalian placental tissue, or any other suitable tissue or fluid from a mammalian donor, (b) is pluripotent; (c) has substantial proliferative potential, (d) optionally, but preferably, does not require feeder cell layers to grow in vitro, and/or (e) optionally, but preferably, specifically binds c-kit antibodies (particularly at the time of collection, as the ability of the cells to bind c-kit antibodies may be lost over time as the cells are grown in vitro).

"Pluripotent" as used herein refers to a cell that has complete differentiation versatility, e.g., the capacity to grow into any of the animal's cell types. A pluripotent cell can be self-renewing, and can remain dormant or quiescent with a tissue. Unlike a totipotent cell (e.g., a fertilized, diploid egg cell) a pluripotent cell cannot usually form a new blastocyst.

"Multipotent" as used herein refers to a cell that has the capacity to grow into any of a subset of the corresponding animal cell types. Unlike a pluripotent cell, a multipotent cell does not have the capacity to form all of the cell types of the corresponding animal.

Cells may be autologous (i.e., from the very subject to which they will be applied) syngeneic (i.e., genetically identical or closely related, so as to minimize tissue transplant rejection), allogeneic (i.e., from a non-genetically identical member of the same species) or xenogeneic (i.e., from a member of a different species). Syngeneic cells include those that are autogenic (i.e., from the subject to be treated) and isogenic (i.e., a genetically identical but different subject, e.g., from an identical twin). Cells may be obtained from, e.g., a donor (either living or cadaveric) or derived from an established cell strain or cell line. For example, cells may be harvested from a donor using standard biopsy techniques known in the art.

According to some embodiments, at least a portion of the cells are viable after they are printed. "Viable cells" includes cells that adhere to a culture dish or other substrate and/or are capable of survival (e.g., proliferation). In some embodiments, at least 30, 40 or 50% of the total cells loaded are viable, and in further embodiments at least 60, 70, 80, or 90% or more of the total cells loaded are viable after printing. Cell viability may be measured by any conventional means, e.g., the MTS assay, and at a reasonable time after printing, e.g., 1 day after printing completion. Viability is measured upon incubation under conditions known in the art to be optimal for survival of the certain cells types present. For example, many eukaryotic cell types are typically incubated in a suitable medium at 5% carbon dioxide (95% atmospheric air) and 37 degrees Celsius.

Various mechanisms may be employed to facilitate survival of the cells during and/or after printing. Specifically, compounds may be utilized that support the printed cells by providing hydration, nutrients, and/or structural support. These compounds may be applied to the substrate using conventional techniques, such as manually, in a wash or bath, through vapor deposition (e.g., physical or chemical vapor deposition), etc. These compounds may also be combined with the cells and/or compositions before and/or during printing, or may be printed or otherwise applied to the substrate (e.g., coated) as a separate layer beneath, above, and/or between cell layers. For example, one such support compound is a gel having a viscosity that is low enough under the printing conditions to pass through the nozzle of the print head, and that can gel to a stable shape during and/or after printing. Such viscosities are typically within the range of from about 0.5 to about 50 centipoise, in some embodiments from about 1 to about 20 centipoise, and in some embodiments, from about 1 to about 10 centipoise. Some examples of suitable gels that may be used in the present invention include, but are not limited to, agars, collagen, hydrogels, etc.

Another polymer used for hydrogels is alginate, a natural polysaccharide extracted from seaweed. One feature of alginate solutions is their gelling properties in the presence of divalent cations (e.g., $Mg^{++}$, $Ca^{++}$, $Sr^{++}$, $Ba^{++}$).

In some embodiments, to promote viability, cells are mixed with the support compound such as a gel shortly before dispensing. For example, cells may be mixed not more than 0.5, 1, 2, 3, 4, 5, 7, 10, 15, 30, 45, 60, 90, or 120 minutes prior to dispensing.

In some embodiments, cells are dispensed to provide about 50,000, 100,000, 150,000, 200,000, 250,000, 300,000, 350,000, 400,000, 450,000, or 500,000 cells per $cm^2$.

Besides gels, other support compounds may also be utilized in the present invention. Extracellular matrix analogs, for example, may be combined with support gels to optimize or functionalize the gel. In some embodiments, one or more growth factors may also be introduced in the printed arrays. For example, slow release microspheres that contain one or more growth factors in various concentrations and sequences may be combined with the cells and/or composition. Other suitable support compounds might include those that aid in avoiding apoptosis and necrosis of the developing structures. For example, survival factors (e.g., basic fibroblast growth factor) may be added. In addition, transient genetic modifications of cells having antiapoptotic (e.g., bcl-2 and telomerase) and/or blocking pathways may be included in compositions printed. Adhesives may also be utilized to assist in the survival of the cells after printing. For instance, soft tissue adhesives, such a cyanoacrylate esters, fibrin sealant, and/or gelatin-resorcinol-formaldehyde glues, may be utilized to inhibit nascent constructs from being washed off or moved following the printing of a layer. In addition, adhesives, such as arginine-glycine-aspartic acid (RGD) ligands, may enhance the adhesion of cells to a gelling polymer or other support compound. Extracellular proteins, extracellular protein analogs, etc., may also be utilized.

"Growth factor" may be any naturally occurring or synthetic growth factor, including combinations thereof, suitable for the particular tissue or array being printed. Numerous growth factors are known. Examples include, but are not limited to, insulin-like growth factor (e.g., IGF-1), transforming growth factor-beta (TGF-beta), bone-morphogenetic protein, fibroblast growth factor, platelet derived growth factor (PDGF), vascular endothelial growth factor (VEGF), connective tissue growth factor (CTGF), basic fibroblast growth factor (bFGF), epidermal growth factor, fibroblast growth factor (FGF) (numbers 1, 2 and 3), osteopontin, bone morphogenetic protein-2, growth hormones such as somatotropin, cellular attractants and attachment agents, etc., and mixtures thereof. See, e.g., U.S. Pat. Nos. 7,019,192; 6,995,013; and 6,923,833. For example, growth factor proteins may be provided in the printed composition and/or encoded by plasmids transfected into printed cells.

In some embodiments, cells, compositions, support compounds, and/or growth factors may be printed from separate nozzles or through the same nozzle in a common composition, depending upon the particular tissue (or tissue substitute) being formed. Printing may be simultaneous, sequential, or any combination thereof. Some of the ingredients may be printed in the form of a first pattern (e.g., an erodable or degradable support material), and some of the ingredients may be printed in the form of a second pattern (e.g., cells in a pattern different from the support, or two different cell types in a different pattern). The particular combination and manner of printing will depend upon the particular tissue being printed.

In some embodiments, cells/compositions are printed onto a substrate, e.g., a biocompatible scaffold, which may be subsequently implanted into or grafted onto a subject in need thereof. In other embodiments, cells/compositions of interest are directly printed in situ onto living tissues in the body, with or without prior substrate application (e.g., a layer of fibrin) in which the cells may attach.

In some embodiments, cells may be isolated from tissues of interest and cultured with techniques known in the art, "Isolated" as used herein signifies that the cells are placed into conditions other than their natural environment. Tissue or cells are "harvested" when initially isolated from a subject, e.g., a primary explant.

The "primary culture" is the first culture to become established after seeding disaggregated cells or primary explants into a culture vessel. "Expanding" or "expansion" as used herein refers to an increase in number of viable cells. Expanding may be accomplished by, e.g., "growing" the cells through one or more cell cycles, wherein at least a portion of the cells divide to produce additional cells. "Growing" as used herein includes the culture of cells such that the cells remain viable, and may or may not include expansion and/or differentiation of the cells.

"Passaged in vitro" or "passaged" refers to the transfer or subculture of a cell culture to a second culture vessel, usually implying mechanical or enzymatic disaggregation, reseeding, and often division into two or more daughter cultures, depending upon the rate of proliferation. If the population is selected for a particular genotype or phenotype, the culture becomes a "cell strain" upon subculture, i.e., the culture is homogeneous and possesses desirable characteristics (e.g., the ability to express a certain protein or marker).

"Express" or "expression" of a protein or other biological marker means that a gene encoding the same of a precursor thereof is transcribed, and preferably, translated. Typically, according to the present invention, expression of a coding region of a gene will result in production of the encoded polypeptide, such that the cell is "positive" for that protein or other downstream biological marker.

"Skin cells" include those cells normally found in skin, and include epidermal cells (e.g., keratinocytes, melanocytes, Merkel cells, Langerhan cells, etc., and any combination thereof) and dermal cells (e.g., fibroblasts, adipocytes, mast cells, macrophages, and any combination thereof). Skin tissue may be formed to mimic natural skin by the inclusion of melanocytes and dermal papilla cells. Skin tissue produced by the process of the present invention is useful for implantation into or on a subject to, for example, treat burns, and other wounds such as incisions, lacerations, and crush injuries (e.g., postsurgical wounds, and posttraumatic wounds, venous leg ulcers, diabetic foot ulcers, etc.).

In some embodiments, skin cells are dispensed as a dermal layer having dermal cells, and an epidermal layer having epidermal cells. In some embodiments, the dermal cells and epidermal cells are provided at a ratio of cell number of about 1:1, or from 5:1 to 1:5, or from 3:1 to 1:3, or from 1:2 to 2:1.

"Muscle cells" include those cells normally found in muscle tissue, including smooth muscle cells, cardiac muscle cells, skeletal muscle cells (e.g., muscle fibers or myocytes, myoblasts, myotubes, etc.), and any combination thereof, Muscle cells/tissues produced by the processes described herein are useful for, among other things, the treatment of injuries or defects affecting muscle tissue, and/or promote muscle healing.

"Cartilage cells" include those cells normally found in cartilage, which cells include chondrocytes. "Chondrocytes" produce and maintain the extracellular matrix of cartilage, by, e.g., producing collagen and proteoglycans. Cartilage is a highly specialized connective tissue found throughout the body, and its primary function is to provide structural support for surrounding tissues (e.g., in the ear and nose) or to cushion (e.g., in the trachea and articular joints). Types of cartilage include hyaline cartilage (articular joints, nose, trachea, intervertebral disks (NP), vertebral end plates), elastic cartilage (tendon insertion site, ligament insertion site, meniscus, intervertebral disks (AP)), costochondral cartilage (rib, growth plate), and fibrocartilage (ear). The loss of cartilage in a subject can be problematic, as it has a very limited repair capacity. "Mesenchymal stem cells" or "MSCs" are progenitors of chondrocytes. MSCs can also differentiate into osteoblasts. Cartilage cells/tissues produced by the processes described herein are useful for, among other things, implantation in a subject to treat cartilage injury or disease.

"Bone cells" include those cells normally found in bone, and include osteoblasts, osteoclasts, osteocytes, and any combination thereof. Bone cells/tissues produced by the processes described herein are useful for, among other things, implantation into a subject to treat bone fractures or defects, and/or promote bone healing.

"Nervous system cells" or "nerve cells" include those cells normally found in the peripheral nervous system, including neuronal and glial cells.

"Vascular cells" include those cells normally found in the mammalian vasculature, including blood vessels, and include endothelial cells, smooth muscle cells and fibroblasts.

In some embodiments, stem cells are printed onto substrates by inkjet printing. Stem cells may be printed alone (typically in combination with a support compound or compounds) or in combination with one or more additional cells (e.g., in a combination selected to produce a tissue as described above). In some embodiments, stem cells are differentiated into cells of interest.

"Differentiation" and "differentiating" as used herein include (a) treatment of the cells to induce differentiation and completion of differentiation of the cells in response to such treatment, both prior to printing on a substrate, (b) treatment of the cells to induce differentiation, then printing of the cells on a substrate, and then differentiation of the cells in response to such treatment after they have been printed, (c) printing of the cells, simultaneously or sequentially, with a differentiation factor(s) that induces differentiation after the cells have been printed, (d) contacting the cells after printing to differentiation factors or media, etc., and combinations of any of the foregoing. In some embodiments, differentiation may be modulated or delayed by contacting an appropriate factor or factors to the cell in like manner as described above. In some embodiments appropriate differentiation factors are one or more of the growth factors described above. Differentiation and modulation of differentiation can be carried out in accordance with known techniques, e.g., as described in U.S. Pat. No. 6,589,728, or U.S. Patent Application Publication Nos.: 2006006018 (endogenous repair factor production promoters); 20060013804 (modulation of stem cell differentiation by modulation of caspase-3 activity); 20050266553 (methods of regulating differentiation in stem cells); 20050227353 (methods of inducing differentiation of stem cells); 20050202428 (pluripotent stem cells); 20050153941 (cell differentiation inhibiting agent, cell culture method using the same, culture medium, and cultured cell line); 20050131212 (neural regeneration peptides and methods for their use in treatment of brain damage); 20040241856 (methods and compositions for modulating stem cells); 20040214319 (methods of regulating differentiation in stem cells); 20040161412 (cell-based VEGF delivery); 20040115810 (stem cell differentiation-inducing promoter); 20040053869 (stem cell differentiation); or variations of the above or below that will be apparent to those skilled in the art.

"Subjects" are generally human subjects and include, but are not limited to, "patients." The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult and geriatric subjects.

Subjects may also include animal subjects or patients, particularly vertebrate animals, e.g., mammalian subjects such as canines, felines, bovines, caprines, equines, ovines, porcines, rodents (e.g., rats and mice), lagomorphs, non-human primates, etc., or fish or avian subjects, for, e.g., veterinary medicine and/or research or laboratory purposes.

"Treat" refers to any type of treatment that imparts a benefit to a subject, e.g., a patient afflicted with a trauma or disease. Treating includes actions taken and actions refrained from being taken for the purpose of improving the condition of the patient (e.g., the promotion of healing and/or formation of tissues on a patient in need thereof, the relief of one or more symptoms, etc.). In some embodiments, treating includes reconstructing skin tissue (e.g., where such tissue has been damaged or lost by injury or disease) by directly printing cells and/or tissues onto a subject in need thereof.

The present invention provides for the printing of tissues by the appropriate combination of cell and support material, or two or three or more different cell types typically found in a common tissue (e.g., skin tissue). Cells, support compounds, and growth factors may be printed from separate nozzles or through the same nozzle in a common composition, depending upon the particular tissue (or tissue substitute) being formed. Printing may be simultaneous, sequential, or any combination thereof. Some of the ingredients may be printed in the form of a first pattern (e.g., an erodable or degradable support material), and some of the ingredients may be printed in the form of a second pattern (e.g., cells in a pattern different from the support, or two different cell types in a different pattern). Again, the particular combination and manner of printing will depend upon the particular tissue. Materials to be printed for specific tissues or tissue substitutes are described further below.

Skin.

In representative embodiments, to produce epidermal-like skin tissue, the following are dispensed:
 (a) at least one cell type, and preferably at least two or in some embodiments three or four different epidermal cell types (e.g., keratinocytes, melanocytes, Merkel cells, Langerhan cells, etc., and any combination thereof); and/or
 (b) at least one support compound such as described above (e.g., collagen, elastin, keratin, etc., and any combination thereof); and/or
 (c) at least one growth factor as described above (e.g., basic fibroblast growth factor (bFGF), Insulin-Like Growth Factor 1, epidermal growth factor (EGF), etc., and any combination thereof);

In some embodiments the epidermal cells, support compound and/or growth factors dispensed as described above (which form an "epidermal" type layer) are printed on, or on top of, a previously formed (e.g., printed or ink-jet printed) "dermal" type layer, the previously printed dermal layer layers comprising: (a) one, two, three or four different dermal cells (fibroblasts, adipocytes, mast cells, and/or macrophages), (b) at least one support compound as described above; and/or (c) at least one growth factor as described above.

Skin tissue produced by the process of the present invention is useful for treatment of, for example, burns, and other wounds such as incisions, lacerations, and crush injuries (e.g., postsurgical wounds, and posttraumatic wounds, venous leg ulcers, diabetic foot ulcers, etc.).

Bone.

In particular embodiments, to produce bone tissues, the following are dispensed:
 (a) at least one bone cell type, and preferably at least two or three different bone cell types (e.g., osteoblasts, osteoclasts, osteocytes, and any combination thereof, but in some embodiments at least osteoblasts and osteoclasts, and in some embodiments all three); and/or
 (b) at least one support compound such as described above (e.g., collagen, hydroxyapatites, calicite, silica, ceramic, proteoglycans, glycoproteins, etc., and any combination thereof); and/or
 (c) at least one growth factor (e.g., bone morphogenetic protein, transforming growth factor, fibroblast growth factors, platelet-derived growth factors, insulin-like growth factors, etc., and any combination thereof).

Bone tissues produced by the processes described herein are useful for, among other things, implantation into a subject to treat bone fractures or defects, and/or promote bone healing.

Nerve.

In representative embodiments, to produce nerve tissue, the following are dispensed:
 (a) at least one, two or three cells types, and preferably (i) peripheral nerve cells and/or (ii) at least one glial cell type and (iii) any combination thereof (e.g., a combination of at least one nerve cell and at least one glial cell); and/or (b) at least one support compound such as described above; (e.g., laminin, collagen type IV, fibronectin, etc., and any combination thereof); and/or (c) at least one growth factor (e.g., NGF, brain-derived neurotrophic factor, insulin-like growth factor-I, fibroblast growth factor, etc., or any combination thereof); and any combination of the foregoing.

Nerve tissue produced by the processes described herein is useful, among other things, to treat nerve injury or degenerative diseases affecting the peripheral nervous system.

Muscle.

In representative embodiments, to produce muscle tissue, the following are dispensed:

(a) at least one muscle cell type; and/or (b) at least one support compound such as described above; (e.g., laminin, collagen type IV, fibronectin, etc., and any combination thereof); and/or (c) at least one growth factor (e.g., vascular endothelial growth factor, insulin-like growth factors (IGFs), etc., or any combination thereof); and any combination of the foregoing.

Muscle tissue produced by the processes described herein is useful, among other things, to treat smooth muscle, skeletal muscle or cardiac muscle injury or diseases affecting these tissues.

Vascular Tissue.

In representative embodiments, to produce vascular tissue, the following are dispensed:

(a) at least one vascular cell type, and preferably at least two or three different vascular cell types (e.g., endothelial cells, smooth muscle cells, fibroblasts, and any combination thereof, but in some embodiments at least endothelial cells, smooth muscle cells, and in some embodiments all three); and/or (b) at least one support compound such as described above; (e.g., laminin, collagen type IV, fibronectin, etc., and any combination thereof); and/or (c) at least one growth factor (e.g., vascular endothelial growth factor, insulin-like growth factors (IGFs), etc., or any combination thereof); and any combination of the foregoing.

Vascular tissue produced by the processes described herein is useful, among other things, to form vascular networks and/or treat injury or diseases affecting these tissues.

In some embodiments, the tissue is created "in sequence" layer-by-layer, with a dispensed layer (A), then a dispensed layer (B), and so on as needed in series, such as layers:

A B C D . . . .

Each layer may comprise cells, support compounds, growth factors, combinations thereof, etc., as desired to construct the tissue as needed or desired.

In some embodiments, cells may be dispensed in a first layer, followed by a second layer of support materials such as a gel, optionally followed by a third layer of cells. For example, a multiple layered skin tissue may be dispensed as a layer comprising fibroblasts, followed by a layer comprising a gel (e.g., comprising fibrin, fibrinogen, collagen, etc.), followed by a layer comprising keratinocytes. Additional layers may also be provided as desired. Thrombin may also be dispensed with or onto one or more layers, if desired.

In some embodiments, skin cells and/or layers thereof can be dispensed (e.g., fibroblasts, keratinocytes, melanocytes, etc.), and additional skin cells printed thereon or therewith in discrete units and/or patterns. For example, papilla cells, which form hair follicles, in some embodiments may be dispensed at specific locations and/or densities (hair shaft thickness and length being at least in part determined by dermal papilla cell number and volume, with hairs becoming longer with increasing cell number), which can generate hair more closely approximating that from the native skin tissue for different body locations, age groups, genders, etc. Outer root cells may also be printed with the dermal papilla cells, if desired. Melanocytes may also be printed at specific locations and/or densities as desired, for example, to better match adjoining skin (e.g., with freckles).

In some embodiments, use of these cell dispensing patterns may also aid in regeneration of old wounds that already have scars, replacing the scars with more natural-looking skin, D. Methods of Data Processing, Computer Programs and Systems.

In some embodiments, data obtained from the optical detector is pieced together to form a model of the surface such as a patient bodily surface of interest (e.g., a wound surface). The bodily surface may be of any body portion, including a hand, foot, arm, leg, torso, chest, abdomen, back, head, face, portions thereof and/or combinations thereof, etc., including a wound area on the same.

In some embodiments, the surface is then transformed into a mold of the surface, A "mold" as used herein is a three-dimensional representation of the surface of interest, which in some embodiments may be displayed visually, and which may also include, in addition to three-dimensional map coordinates, information such as color and/or infrared radiation intensity, among others. The mold according to some embodiments may be interpreted into a "negative" mold, in which the layers are reversed, and may be further split into layers on the Z axis to determine which layers correspond to the natural tissue layers (e.g., dermis and epidermis layers of skin tissue), as necessary to guide the associated dispenser.

In some embodiments, each layer is overlaid with a series of lines (i.e., the lines are added to the layer representation or mold) that cover at least a portion of the area detected. These lines may then be used (e.g., by control software) to determine a path for the dispensing system. The dispensing system may dispense along the series of lines for each layer, thus forming a tissue in a layer-by-layer fashion.

In some embodiments, the user can define a series of bitmap images where each non-black pixel corresponds to a cell drop, and the color of the pixel corresponds to the cell type to print. This allows the user to create complex structures using various cell types and/or in various configurations.

System and/or component operation according to some embodiments may be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the desired operations.

These computer program instructions may also be stored in a computer-readable memory that can direct a computer or other programmable data processing apparatus to function in a particular manner, such that the instructions stored in the computer-readable memory produce an article of manufacture including instructions which implement the operations.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the operations.

Accordingly, the present invention may be embodied in hardware and/or in software (including firmware, resident software, micro-code, etc.). Furthermore, embodiments of the present invention may take the form of a computer program product on a computer-usable and/or computer-readable storage medium having computer-usable or computer-readable program code embodied in the medium for use by or in connection with an instruction execution system. As used herein, a computer-usable or computer-readable medium may be any medium that can contain or store the program for use by or in connection with the instruction execution system, apparatus, or device.

The computer-usable and/or computer-readable medium may be, for example, but not limited to, an electronic, magnetic, optical, electromagnetic, infrared, or semiconductor system, apparatus or device. More specific examples (a non-exhaustive list) of the computer-readable medium would include the following: a portable computer diskette, a random access memory (RAM), a read-only memory (ROM), an erasable programmable read-only memory (EPROM or Flash memory), and a portable compact disc read-only memory (CD-ROM).

In some embodiments, software employs a three-tiered architecture design. The three-tiered architecture handles three areas of communication: between the user and the software; among the software components; and between the software and the file system. This design structure may allow individual components to be quickly and easily altered as necessary without affecting the other components.

In some embodiments, data gathered from the optical detector are represented as an object (e.g., a skin object). Each object may comprise one or more layers of the tissue, and each layer may be broken into a grid that encapsulates the individual lines from detector. This representation may significantly reduce the time necessary to deliver/dispense skin by allowing the delivery/dispensing system to print points from one piece of the grid while the computer analyzes the next piece. In some embodiments, points from the object are passed in a generic format to the delivery system where they are parsed for use by the dispensing system in a manner that incorporates the locations of the different cell types in the printhead and/or catridge. This implementation may allow the user to quickly define enhancements to the scanned data and include other components of the tissue (e.g., skin components such as melanocytes and hair follicles for skin tissue).

In some embodiments, the architecture may be based on the Microsoft .NET Framework (e.g., .Net Framework version 1.0, 1.1, 2.0, 3.0, 3.5, or 4.0) (Microsoft Corp., Redmond, Wash.) or other software libraries or programming languages. Some embodiments provide that the software may be written in any one or combination of programming languages, including object-oriented programming languages such as, for example, C++, among others. The three-tiered architecture may be configured to handle three areas of communications: between the user and the software; among the software components; and between the software and the file system. This design structure may allow every component to be quickly and easily altered as necessary without affecting the other components. Furthermore, in some embodiments the software is not based on a proprietary system such as, for example, MATLAB®, so that it can be deployed to a wide range of computers, such as any computer capable of running the .NET Framework.

In some embodiments, an interpreter or interface module is provided between the dispensing system software and a database. For example, an interpreter/interface module may expose methods for combining semantics from the database and data from a scanning system. In one example, the interpreter may be used to assign Z layers to a dermis or an epidermis. In other words, Z layers below a certain point could be assigned to the dermis, and Z layers above that point could be assigned to the epidermis. These different skin structures may require different cell types, and such cell type data may be stored in the database and accessed by the interpreter. In another example, the interpreter may be used to combine data from multiple imaging systems into a standardized data set. In other words, infrared or ultrasound imaging techniques may be combined with a wound map.

The interpreter may convert data received from the scanning system and/or stored in the database into a different format. For example, the interpreter may convert the data from the scanning system and/or in the database into a standardized format. The database may include semantics corresponding to the dispensing system software, the scanning system, and/or the manipulator. For example, the interpreter may use the semantics from the database to convert data received from the scanning system and/or the manipulator into a standardized format that is recognized by the dispensing software. Semantics may include various rules, such as rules regarding colors in a color range and the correspondence of the colors to poor vascularization (e.g., to represent areas where growth factors may be delivered). Other examples of rules include rules regarding non-viable tissue detected by infrared imaging (e.g., to represent tissue that may be excised). Further examples of rules include rules regarding hair follicles (e.g., to indicate a point below which the hair follicles should be delivered in Z layers).

The standardized format that may be produced by the interpreter is recognized by, and operable with, the dispensing system software without having to re-write the dispensing system software. Accordingly, the interpreter may be used to update/upgrade the scanning system and/or the manipulator. In another example, the interpreter may convert data received from the manipulator software into a format recognized by the delivery/dispensing system. Additionally, in some embodiments, the interpreter may be used during operations (e.g., scanning and/or dispensing) of the scanning system and/or the dispensing system, for example, for cell/composition delivery to a subject.

Figure 13:
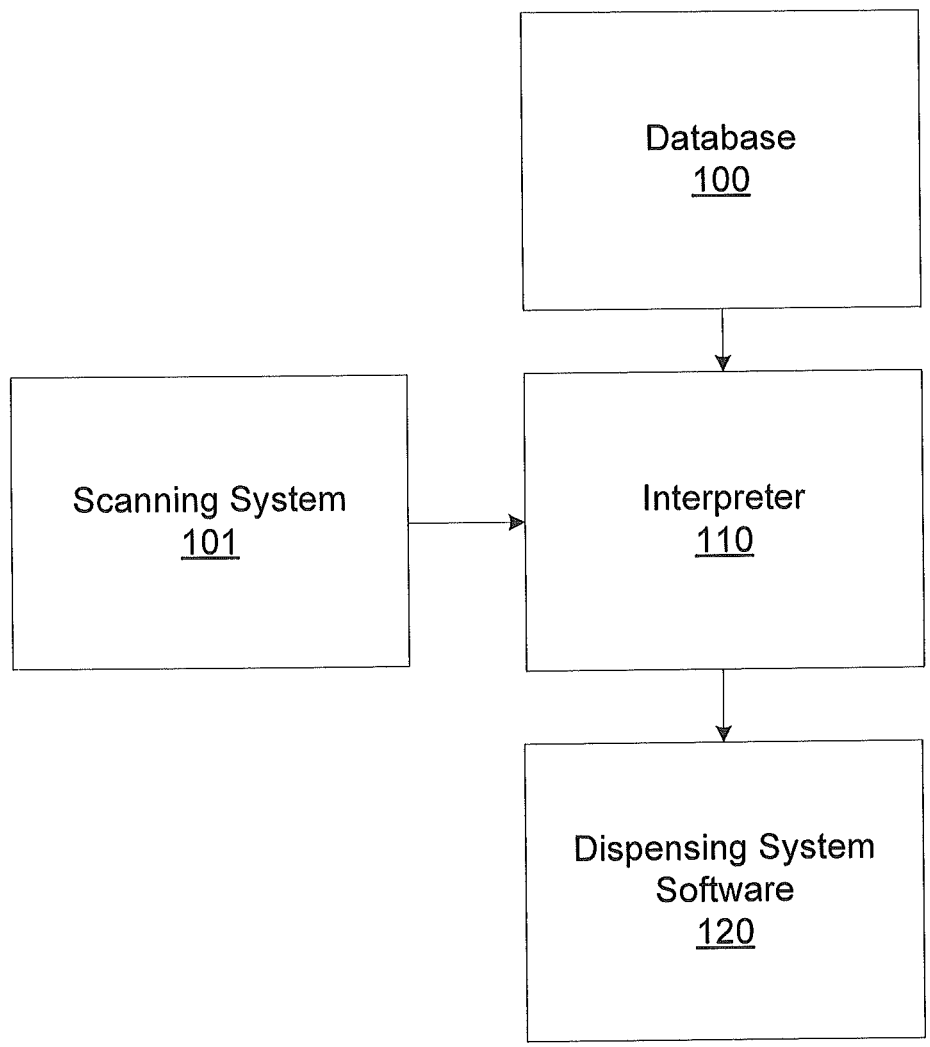
FIG. 13 is a diagram of a scanning system (101) communicating with an interpreter (110).

In an example using the interpreter with the scanning system, image data (e.g., raw image data generated by a scanner) may be transferred from the scanning system to an object (e.g., the interpreter). The object/interpreter may then convert the data into the standardized format. For example, referring to FIG. 13, an interpreter (110) receives data from a database (100) and/or from a scanning system (101). The interpreter (110) may then convert the received data into a format recognized by dispensing system software control module (120). The data received from the scanning system (101) may include spectral analysis data, ultraviolet light data, natural interaction data (e.g., data corresponding to control of the delivery system with human movements, such as manipulating a position of the dispenser system output by using human hands to direct its movement without touching the system), ultrasound data, reflectance data (e.g., data corresponding to light reflected from an object), scanner data, and/or other data that may be generated by optical detectors described herein. Accordingly, new imaging technologies may be rapidly incorporated into the scanning system (101) and the dispensing system software (120). For example, the interpreter (110) allows improvements/upgrades (e.g., a new camera or optical sensor) to the scanning system (101) without upgrading the dispensing system software (120). In particular, the interpreter (110) allows improvements to the scanning system (101), without re-writing the dispensing system software (120), by storing semantics associated with the improvements in the database (100).

One example of extending the scanning system (101) without re-writing the dispensing system software (120) is integrating the Kinect® system from the Microsoft Corporation (Redmond, Wash.) into the scanning system (101). For example, the Kinect® may provide infrared and visible light imaging at 30 frames/second, and may thus be used as the optical sensor (11) in FIG. 2 to provide imaging (e.g., depth imaging) for the scanning system (101). Open source drivers for the Kinect® and/or various application programs for the Kinect® may be added to the database (100). Accordingly, the Kinect® may be integrated into the scanning system (101) without re-writing the dispensing system software (120).

Figure 14:
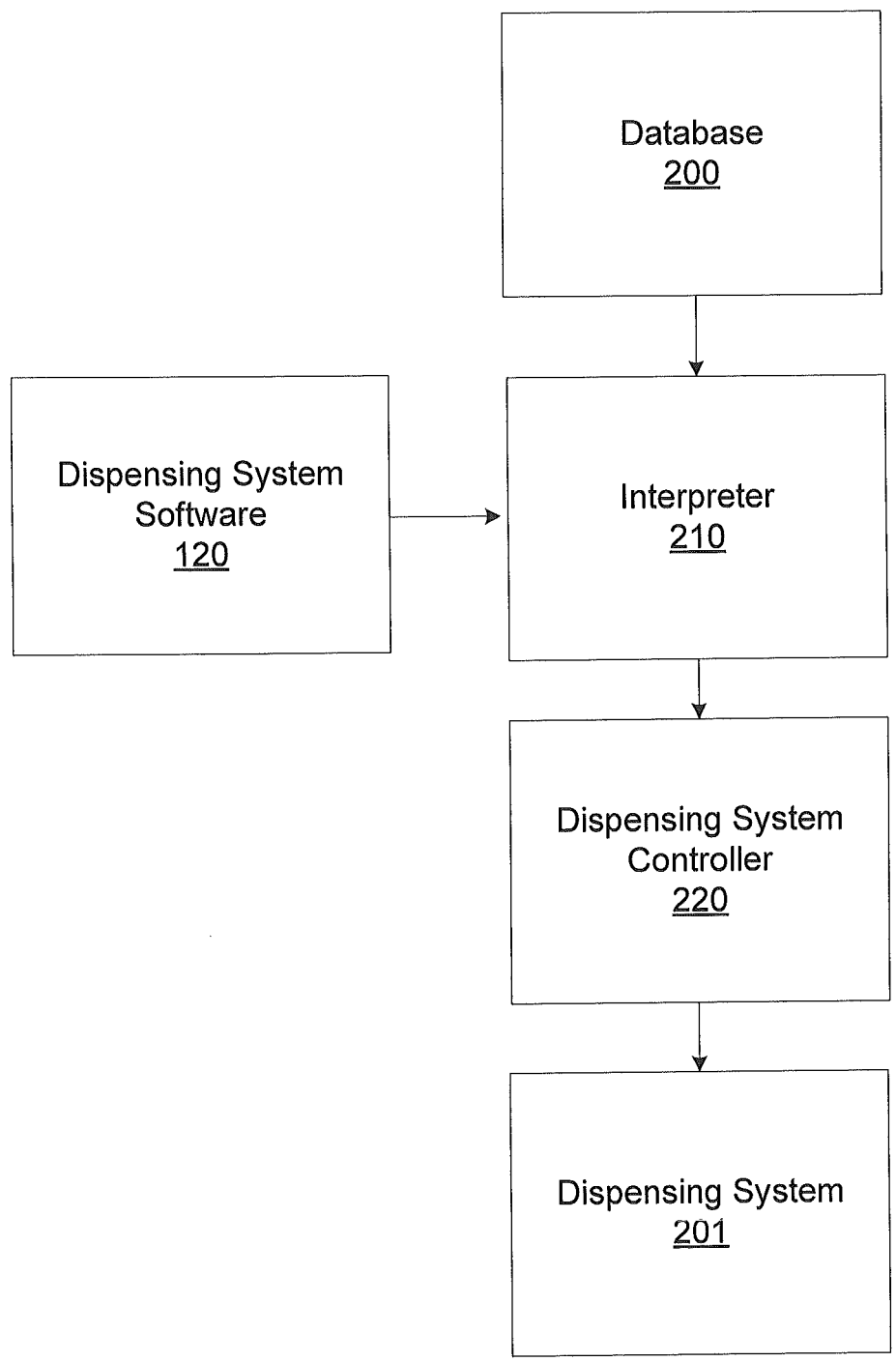
FIG. 14 is a diagram of a dispensing system (201) communicating with an interpreter (210).

In some embodiments in which the dispensing system includes an interpreter, the database may include cartridge data. For example, referring to FIG. 14, parameters (e.g., data corresponding to cartridge software/device drivers, cartridge chemical/biological contents, cartridge volume levels/capacities, cartridge fill dates, cartridge content expiration dates, cartridge nozzles, and/or cartridge flow rates) for one or more cartridges may be stored in a database (200). As such, a library of dispensing system parameters may be included in the database (200). For example, the library of parameters enables the addition of new cell types or biomaterials without hard-coding parameters in the dispensing system software (120). Accordingly, adding, for example, a new cell type to the dispenser may only require adding a plug-in to the library of dispensing system parameters in the database (200).

In some embodiments, cartridge parameters may include semantics rules. For example, cartridge parameters may include rules that direct scarless healing reagents to be dispensed only on a wound edge. In other example, cartridge parameters may include rules that direct vascular growth factors to be dispensed only in areas marked by the interpreter. In a further example, cartridge parameters may include rules regarding cell densities for dispensing.

An interpreter (210) receives cartridge data from the database (200) and then converts the received data into a format used by the dispensing system software (120) and/or the dispensing system (201). In some embodiments, the dispensing system interpreter (210) converts data into the same format as the scanning system interpreter (110). Additionally, in some embodiments, a dispensing system controller (220) is connected between the interpreter (210) and the dispensing system (201). As such, the interpreter (210) may convert data into a format that is recognized by the dispensing system controller (220).

The database (200) may be updated to include data for any form of therapy (e.g., any cell type, reagent, macromolecule, and/or biomaterial) that can be packaged into a cartridge. The database (200) may be updated directly by a database user (e.g., via manual data entry or a storage device), by connecting to another cartridge database (e.g., a cartridge manufacturer's database), and/or by accessing data stored on/in a cartridge. In some embodiments, the database (200) may be automatically updated in response to connecting a new cartridge, or an existing cartridge with new contents, to the dispensing system (201). For example, the database (200) may connect with another database and/or may download information stored on/in the cartridge to automatically update the database (200) in response to connecting the cartridge. As such, additional forms of therapy (e.g., via new cartridges or existing cartridges with new contents) may be incorporated into the dispensing system (201) by updating the database (200), and without re-writing the dispensing system software (120).

Figure 15:
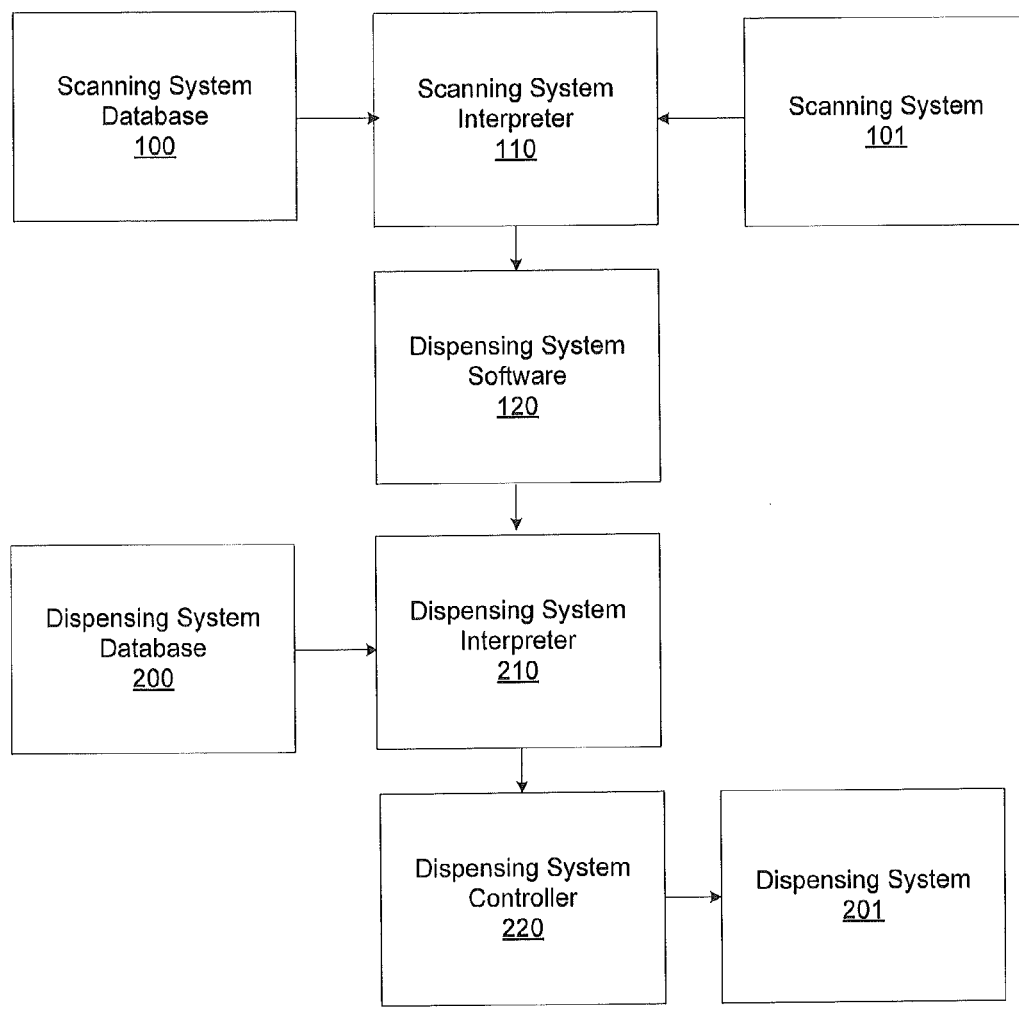
FIG. 15 is a diagram of scanning system (101) and dispensing system (201) communicating with interpreters (110, 210).

Referring to FIG. 15, one or more interpreters (110, 210) may be provided for the scanning system (101) and the dispensing system (201). For example, the scanning system interpreter (110) may be connected between the scanning system (101) and the dispensing system software (120), and the dispensing system interpreter (210) may be connected between the dispensing system (201) and the dispensing system software (120). Alternatively, a single interpreter may function as both the scanning system interpreter (110) and the dispensing system interpreter (210). In some embodiments, the scanning system interpreter (110) communicates with the scanning system database (100), and the dispensing system interpreter (210) communicates with a dispensing system database (200). Alternatively, single database may include both the scanning system database (100) and the dispensing system database (200).

In some embodiments, the dispensing system software (120) may control the dispensing system (201) in response to a conversion by the scanning system interpreter (110) of scanning system data into a standardized format. For example, the scanning system interpreter (110) may convert data into the standardized format in response to operating the scanning system (101) (e.g., performing a scanning operation with the scanner). Moreover, the dispensing system software (120) receives the standardized format data from the scanning system interpreter (110). Thus, in response to using the scanning system (101), the dispensing system software (120) may command the dispensing system (201) to deliver a particular form of therapy using a cartridge. The dispensing system interpreter (210) may receive commands, among other data, from the dispensing system software (120), and may receive data from the dispensing system database (200). The dispensing system interpreter (210) may format the data received from the biodispensing software (120) and the dispensing system database (200), and may provide the formatted data to the dispensing system (201). In some embodiments, the dispensing system controller (220) may receive the formatted data from the dispensing system interpreter (210). The dispensing system controller (220) may then use the formatted data to operate the dispensing system (201). Accordingly, the dispensing system software (120) may operate the dispensing system (201) in response to the standardized format data received by the dispensing system software (120) from the scanning system interpreter (110).

In alternative embodiments, the dispensing system software (120) may communicate directly with the scanning system (101) instead of communicating through the scanning system interpreter (110). Updating the scanning system (101) in such embodiments, however, may require re-writing the dispensing system software (120).

In further alternative embodiments, cartridge parameters may be directly written into the dispensing system software (120) instead of writing the parameters in the dispensing system database (200). As such, new cartridges, or new contents for existing cartridges, may require re-writing the dispensing system software (120).

The present invention is explained in greater detail in the following non-limiting examples.

EXAMPLES

This example describes the design and use of a novel delivery system for in situ bioprinting of the skin. The cartridge based system presented here can be easily transported from patient to patient and can rapidly print skin constructs that mimic normal skin. The device allows for rapid on-site management of burn wounds, integrating a method to determine the size, shape, and depth of a wound with controlled delivery of skin cells to the target wound site in situ. This integration allows the system to effectively manage the treatment of large injuries while reconstructing the normal skin structure. A proof-of-concept experiment using in situ delivery of fibroblasts and keratinocytes to a mouse model of large skin wounds described below demonstrates its efficacy.

Materials and Methods

The following criteria were established to guide the hardware design for this exemplary system:
1. The system should be portable and capable of being quickly transported to the wounded personnel and it should be easily converted for use in different patients with different needs. For example, the system should be capable of fitting through hospital doors and hallways, and it should be constructed from lightweight materials for easy transport.
2. The system should be capable of easy sterilization.
3. The system should be capable of tailoring cell therapy to a patient's specific needs.
4. The system should allow for a wide range of body types.
5. The system should be capable of repeated use.
6. Maintenance of the system should be relatively easy and inexpensive.

We have accomplished these goals by using a cartridge based delivery system with a laser scanning system, both mounted on a portable XYZ plotting system (see FIG. 1). The cartridge system is similar to that used in traditional inkjet printing such that each cell type is loaded into an individual cartridge in the same way different color inks would be contained in different cartridges. However, standard inkjet printing connects one printhead to one cartridge, while the skin delivery/dispensing system allows each cartridge to connect to multiple printheads. This type of configuration allows arbitrary printhead configurations that can conform to each patient's specific needs. It also increases the throughput of the system and provides a rapid method of sterilization by attaching a cartridge of cleaning fluid to the printheads.

The printheads in the device use pressure-based nozzles instead of the thermal or piezoelectric microfluidic delivery devices used in traditional inkjet printers. A pressure-based delivery/dispensing system allows the printer to remain a safe distance above the patient to accommodate a variety of body types.

Tailoring cell therapy to individual patients requires length, width, and depth information about the wound. This system incorporates a three-dimensional laser scanner (NextEngine Inc., Santa Monica, Calif.) mounted above the patient. This scanner can be moved to various locations on the body, and information about the wound is gathered with an accuracy of approximately 127 µm.

The cartridges, printheads, and scanner are mounted on the Z axis of a belt-driven plotting system (see FIG. 1) capable of 100 µm movements. The Y axis moves the X axis which in turn moves the Z axis. Since the X and Y axes comprise the majority of the system's weight this configuration allows those axes to remain stationary while permitting the system to accommodate a wide range of body types.

The plotting system is mounted on a mobile frame. Patients with massive burn injuries are difficult to transport and some current treatments, including INTEGRA® and autologous keratinocyte culture, require multiple procedures. Multiple procedures require the fragile patient to be moved between the bed and the operating room for a number of times. This frame is designed to alleviate transport concerns by allowing the system to quickly move to patient beds and operating rooms.

Methods of Data Processing, Computer Programs and Systems

The skin delivery/dispensing system is controlled by software employing a three-tiered architecture design based on the Microsoft .NET Framework (Microsoft Corp., Redmond, Wash.) and was written in C++. The three-tiered architecture handles three areas of communication: between the user and the software, among the software components, and between the software and the file system. This design structure allows every component to be quickly and easily altered as necessary without affecting the other components. Furthermore, because the software is not based on a proprietary system such as MATLAB®, it can be deployed to any computer capable of running the .NET Framework.

The data obtained from the laser scanner is pieced together to form a model of the wound surface. This surface is transformed into a negative mold of the wound which is split into layers on the Z axis to determine which layers correspond to the dermis and epidermis. Each layer is overlaid with a series of lines that cover the entire wound area. These lines are used by the control software to determine a path for the printer.

Each of the smaller components of the software follows a design pattern similar to the overall architecture. Data gathered from the laser scanner are represented as a skin object. Each skin object consists of skin layers, and each layer is broken into a grid that encapsulates the individual lines from the scanner. This representation significantly reduces the time necessary to deliver/dispense skin by allowing the delivery/dispensing system to print points from one piece of the grid while the computer analyzes the next piece. Points from the skin object are passed in a generic format to the delivery/dispensing system where they are parsed for printing in a manner that incorporates the locations of the different cell types in the printhead. This implementation allows the user to quickly define enhancements to the scanned data and include other important skin components such as melanocytes and hair follicles.

The interpreter/interface module is provided between the dispensing system software and the database. The interpreter converts data received from the scanning system and/or stored in the database into a different format. The database includes semantics corresponding to the dispensing system software, the scanning system, and/or the delivery/dispensing system. The interpreter may thus use the semantics from the database to convert data received from the scanning system and/or the delivery/dispensing system into a standardized format that is recognized by the dispensing system software. The semantics include various rules, such as rules regarding locations where dispensing system treatments should be delivered.

The standardized format that may be produced by the interpreter is recognized by, and operable with, the dispensing system software without having to re-write the dispensing system software. Accordingly, the interpreter may be used to update/upgrade the scanning system and/or the delivery/dispensing system. Moreover, the interpreter may convert data received from the dispensing system software into the format recognized by the delivery/dispensing system. Additionally, the interpreter may be used during operations (e.g., scanning and/or printing) of the scanning system and/or the delivery/dispensing system, for example, for cell/composition delivery/dispensing.

Image data (e.g., raw image data generated by the scanner) may be transferred from the scanning system to the interpreter. The interpreter may then convert the data into the standardized format. For example, referring to FIG. 13, the interpreter (110) receives data from the database (100) and/or from the scanning system (101). The interpreter (110) may then convert the received data into the format recognized by delivery/dispensing system software control module (120). Accordingly, new imaging technologies may be rapidly incorporated into the scanning system (101) and the dispensing system software (120). For example, the interpreter (110) allows improvements/upgrades (e.g., a new camera or optical sensor) to the scanning system (101) without upgrading the delivery/dispensing system software (120). In particular, the interpreter (110) allows improvements to the scanning system (101), without re-writing the delivery/dispensing system software (120), by storing semantics associated with the improvements in the database (100).

One example of extending the scanning system (101) without re-writing the delivery/dispensing system software (120) is integrating the Kinect® system from the Microsoft Corporation (Redmond, Wash.) into the scanning system (101). For example, the Kinect® may provide infrared and visible light imaging at 30 frames/second, and may thus be used as the optical sensor (11) in FIG. 2 to provide imaging (e.g., depth imaging) for the scanning system (101). Open source drivers for the Kinect® and/or various application programs for the Kinect® may be added to the database (100). Accordingly, the Kinect® may be integrated into the scanning system (101) without re-writing the delivery/dispensing system software (120).

In another example, a ZScanner® from 3D Systems, Inc, (Rock Hill, S.C.) may be integrated into the scanning system (101). For example, a ZScanner® may provide handheld, self-positioning 3D scanning (e.g., high-resolution reproductions of complex organs and bone structures), and may thus be used as the optical sensor (11) in FIG. 2 to provide imaging for the scanning system (101). As an example, a ZScanner® may be used with software packaged therewith (e.g., Geomagic® software (Research Triangle Park, North Carolina)) to scan a human hand for an image of the hand and to obtain the surface area and depth of the hand. Additionally, the scanning provided by a ZScanner® may include real-time surfacing that visualizes/indicates scanning progress while scanning a human patient. Accordingly, a ZScanner® may be integrated into the scanning system (101), either additionally or alternatively to integrating the Kinect® system into the scanning system (101).

The database may include printer cartridge data. As such, the library of biodispensing parameters may be included in the database (200). For example, the library of parameters enables the addition of new cell types or biomaterials without hard-coding parameters in the delivery/biodispensing software (120). Accordingly, adding, for example, a new cell type to the dispenser may only require adding a plug-in to the library of biodispenser parameters in the database (200). Additionally, cartridge parameters may include semantics rules, such as rules for directing treatment to be dispensed only on certain portions of a wound or other portions of a body, or rules regarding cell densities for delivery/dispensing.

The interpreter (210) receives printer cartridge data from the database (200) and then converts the received data into a format used by the delivery/dispensing system software (120) and/or the delivery/dispensing system (201). Additionally, the delivery/dispensing system controller (220) is connected between the interpreter (210) and the delivery/dispensing system (201). As such, the interpreter (210) may convert data into a format that is recognized by the delivery/dispensing system controller (220).

The database (200) may be updated to include data for any form of therapy (e.g., any cell type, reagent, macromolecule, and/or biomaterial) that can be packaged into a printer cartridge. The database (200) may be updated directly by the database user (e.g., via manual data entry or a storage device), by connecting to another printer cartridge database (e.g., a printer cartridge manufacturer's database), and/or by accessing data stored on/in a printer cartridge. For example, the database (200) may be automatically updated in response to connecting a new printer cartridge, or an existing printer cartridge with new contents, to the delivery/dispensing system (201). In particular, the database (200) may connect with another database and/or may download information stored on/in the printer cartridge to automatically update the database (200) in response to connecting the printer cartridge. As such, additional forms of therapy (e.g., via new printer cartridges or existing printer cartridges with new contents) may be incorporated into the delivery/dispensing system (201) by updating the database (200), and without re-writing the delivery/dispensing system software (120).

Referring to FIG. 15, one or more interpreters (110, 210) may be provided for the scanning system (101) and the delivery/dispensing system (201). For example, the scanning system interpreter (110) may be connected between the scanning system (101) and the delivery/dispensing system software (120), and the dispensing system interpreter (210) may be connected between the delivery/dispensing system (201) and the delivery/dispensing system software (120).

The delivery/dispensing system software (120) may control the delivery/dispensing system (201) in response to a conversion by the scanning system interpreter (110) of scanning system data into the standardized format. For example, the scanning system interpreter (110) may convert data into the standardized format in response to operating the scanning system (101) (e.g., performing a scanning operation with the scanner). Moreover, the delivery/dispensing system software (120) receives the standardized format data from the scanning system interpreter (110). Thus, in response to using the scanning system (101), the delivery/dispensing system software (120) may command the delivery/dispensing system (201) to deliver a particular form of therapy using a printer cartridge. The delivery/dispensing system interpreter (210) may receive commands, among other data, from the delivery/dispensing system software (120), and may receive data from the delivery/dispensing system database (200). The delivery/dispensing system interpreter (210) may format the data received from the delivery/dispensing system software (120) and the delivery/dispensing system database (200), and may provide the formatted data to the delivery/dispensing system (201). The delivery/dispensing system controller (220) may receive the formatted data from the delivery/dispensing system interpreter (210). The delivery/dispensing system controller (220) may then use the formatted data to operate the delivery/dispensing system (201). Accordingly, the delivery/dispensing system software (120) may operate the delivery/dispensing system (201) in response to the standardized format data received by the delivery/dispensing system software (120) from the scanning system interpreter (110).

Animal Model and Testing

All animal procedures were performed according to the protocols approved by the Wake Forest University Health Sciences Animal Care and Use Committee. The skin delivery system prototype was evaluated by creating a 3×2.5 cm (L×W) full-thickness skin defect on the dorsa of six female outbred athymic nude (Nu/nu) mice (Charles River Laboratories, Raleigh, N.C.). This defect represents approximately a 50% TBSA wound. Three mice were untreated and the others were treated by cell printing. Human fibroblasts were obtained from human foreskin and cultured in high glucose Dulbecco's modified Eagle's medium (Gibco-BRL, Grand Island, N.Y.) with 5% fetal bovine serum and 1% antibiotics. Human keratinocytes were obtained from ScienCell (Carlsbad, Calif.) and cultured in keratinocyte serum-free media (Gibco-BRL) with 1% antibiotics. When sufficient cell numbers were reached, cells were trypsinized for 5 min and suspended in a mixture of 25 mg/mL fibrinogen and 1.1 mg/mL type I collagen in phosphate-buffered saline. One layer of fibroblasts (passage 6) was printed at 250,000 cells $cm^{-2}$ followed by an equal amount of 20 IU/mL thrombin. The thrombin was allowed to react for 15 minutes before a layer of keratinocytes (passage 5) was printed at 500,000 cells $cm^{-2}$, again followed by thrombin. Each wound received antibiotic cream and was covered with sterile cotton gauze wrapped in surgical tape to prevent removal by the mouse. Wound coverings were changed at 1 week and removed at 2 weeks post-surgery. Fibroblasts and keratinocytes given to one mouse were prelabeled with the fluorescent dyes PKH 26 (red) and PKH67 (green) (Sigma-Aldrich, St. Louis, Colo.), and this mouse along with one untreated mouse were sacrificed at 1 week for retrieval of the wound area to determine if the labeled cells were present in the construct. The wound size for the experiment with labeled cells was 1.5×2 cm (L×W) for proof of concept. For the other two mice, each 3×2.5 cm wound was evaluated every week for 3 weeks to determine the size of the wound and the extent of scarring. At 3 weeks the scar tissue was removed for histological evaluation.

Results

Figure 9:
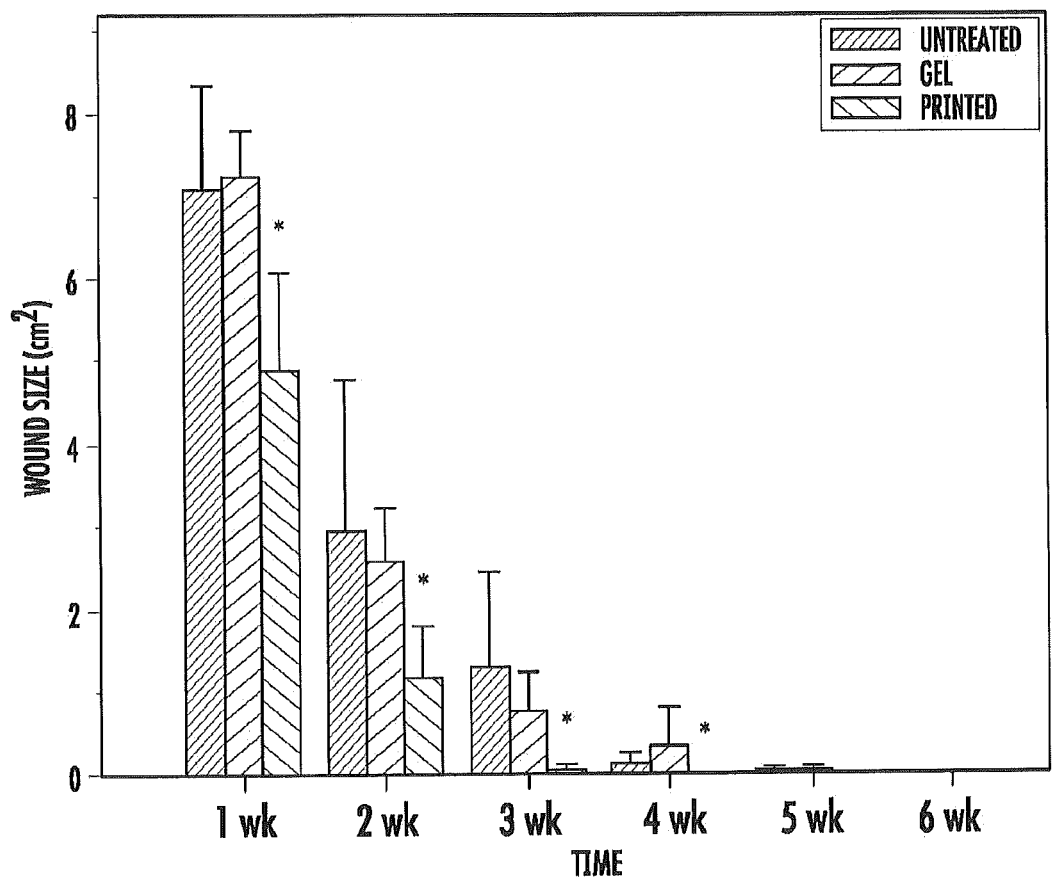
FIG. 9 is a graph of experimental results demonstrating that skin repair using bioprinting shows significant difference in wound size between 1 and 4 weeks after injury ($p<0.05$).

The skin delivery system is capable of printing skin cells directly onto a full-thickness defect on nude mice. Skin constructs printed with fluorescent prelabeled cells and retrieved after 1 week showed the presence of labeled cells within the wound bed (data not shown). These cells appeared to participate in the healing process, as near-complete closure of the wound occurred at 2 weeks, and complete wound closure occurred at 3 weeks (data not shown). H&E staining of the skin constructs at 3 weeks demonstrated structural similarity to normal skin, with organization of the keratinocytes into epidermal strata and the fibroblasts into dermis (data not shown). The untreated mouse showed wound healing in the same timeframe but did not demonstrate complete wound closure as seen in the printed mice. In addition, the center of the untreated wound shows inflammation and scabbing at 3 weeks whereas the covered wound shows cellular integration into the surrounding skin. Results are shown in FIG. 9.

Discussion

The skin delivery system allows rapid production of patient-specific wound coverage while simultaneously obviating the need for specialized manufacturing facilities and cell culture materials at burn care centers. Furthermore, the delivery system fulfills many of the criteria for an ideal skin substitute as demonstrated by previous uses of allogeneic skin cells for burn coverage. Cells printed using the delivery system adhere intimately to the wound bed, provide a non-antigenic microbial barrier, participate in normal host repair mechanisms, maintain elasticity and long-term durability, display long-term mechanical and cosmetic function comparable to split-thickness autografts, require a single operation, are inexpensive, and have minimal storage requirements. The only ideal skin substitute characteristic that is not fulfilled by this system is the requirement of indefinite storage, which is virtually impossible to achieve with any living skin substitute. However, the cartridge system allows packing and shipping of allogeneic cells to burn centers, which in turn allows treatment of the wound as soon as the patient is stable and the wound has undergone debridement. In contrast, a typical autologous graft requires 2-5 weeks to grow in culture.

Proof-of-concept was demonstrated by printing a two-layer skin construct consisting of fibroblasts and keratinocytes directly into a full-thickness skin defect on a nude mouse. This printing was performed by delivering specific cells to specific target areas.

The cells were in a matrix of fibrinogen and type I collagen for two reasons. First, the formation of fibrin from the reaction of fibrinogen and thrombin provides a strong gel that allows the cells to maintain their position on the mouse even if the mouse moves. Second, fibrin and type I collagen have already been used to create skin constructs. After printing, prelabeled fibroblasts and keratinocytes were visible in the construct 1 week post-printing, indicating that the cells remained in the wound area. Evaluation of the wound area over 3 weeks showed rapid closure of the wound in the treated mouse as compared to the untreated mouse. The remaining open wound in the printed group at 2 weeks post-surgery was open only at the center of the wound in the area of greatest body curvature. This could be due to the possibility that the printed cell droplets rolled off the curvature. One way to correct for this may be by replacing the thrombin delivery system with a nebulizer to rapidly create fibrin.

H&E staining of the printed constructs showed organization of the cells into a structure similar to normal skin. The epidermis was the same thickness in both the printed construct and normal tissue. There was a demarcation at the dermal-epidermal junction and the dermis in the printed construct appeared to be similar in composition to the normal tissue. This shows the ability of the skin delivery system to print tissue that mimics the normal skin structure.

While this study only examined the use of fibroblasts and keratinocytes in skin printing, the design of the system allows for precise delivery of additional cell types. These include, but are not limited to, follicular cells, melanocytes, and endothelial cells. Including these additional cell types could further mimic the normal skin structure and provide functional and cosmetic improvements over current treatment techniques, especially with regard to pigmentation and vascularization. The print cartridges can also be designed to include factors aimed at improving the function of the skin constructs. These include scarless healing reagents, growth factors, and protease inhibitors to maintain the longevity of other reagents. If a cell type or reagent can be packaged into a cartridge, our system can rapidly deliver that cell or reagent to a specific location on the patient. This property makes the system superior to most current burn treatments because it eliminates the need for culturing cells and reagents in a graft construct prior to patient transplantation.
Additional Testing in a Porcine Model Prior to bioprinting a small portion of partial thickness skin was removed from each pig. The dermis and epidermis were digested to isolate fibroblasts and keratinocytes for autologous wound repair. Porcine fibroblasts and keratinocytes isolated from additional pigs were used for allogeneic repair. Cells were embedded in a matrix of 20 mg/mL fibrinogen/1.0 mg/mL type I rat tail collagen prior to bioprinting. During printing this matrix was cross linked using atomized thrombin.

Four full thickness excisional wounds were made on the dorsa of 3 female Yorkshire pigs. These wounds were 10 cm×10 cm and were sited in the same area of the dorsum to eliminate confounding from differences in healing from different wound sites. Each wound received a different treatment—untreated, matrix-only, allogeneic repair using fibroblasts and keratinocytes, and autologous repair using fibroblasts and keratinocytes. 10 million fibroblasts and 10 million keratinocytes were printed in both the autologous treatment and the allogeneic treatment. Bioprinted cells were pre-labeled with CM-DiI, a red fluorescent protein that intercalates in the cell membrane. CM-DiI is non-toxic to cells and does not photobleach. Each wound was scanned with the laser scanner and the resulting map was used to print the skin that was missing with both a dermis of fibroblasts and an epidermis of keratinocytes.

The laser scanner collected data that was converted to create a map for bioprinting. This guides the printhead in the bioprinting. Four inkjet valves were used to deliver fibroblasts and keratinocytes and two atomizers were used to deliver thrombin for crosslinking fibrinogen.

Treatment with allogeneic cells was able to close the wound more quickly than negative controls, and showed no statistically significant difference in epithelialization over negative controls. Wounds treated with fibrin/collagen alone and wounds that received no treatment did not achieve wound coverage at 8 weeks.

Autologous keratinocytes showed evidence of re-epithelialization in the wound center at 2 weeks post-printing. These areas of epithelialization grew progressively larger until they had covered the entire wound. Allogeneic keratinocytes, while visible in the wound, did not show the same epithelialization response. It is possible that the culture of allogeneic keratinocytes contained antigen-presenting cells that interfered with the regeneration of the epidermis.
Subsequent Additional Testing in Porcine Model Materials and Methods:

Skin fibroblasts and keratinocytes were isolated from the dorsum of porcine skin through a partial thickness skin biopsy of (0.015 inch). A cell isolation and culturing protocol of fibroblast and keratinocytes was developed to improve the cell yield and viability in cultures. Cells were washed with 10 vol. % of antibiotic-antimycotic (ABAM) twice for 5 minutes each and then with 1 vol. % ABAM twice for 5 minutes. The skin biopsies were then immersed in Dispase II solution for 16 hours to facilitate the disassociation of dermis from epidermis. Upon disassociation, epidermis and dermis were washed extensively with PBS and then minced. Keratinocytes were obtained from the epidermis through digestion in trypsin for 20 minutes at 37 C. Fibroblasts were obtained by digestion in collagenase for 15 minutes at 37 C. Fibroblasts were then cultured in High glucose DMEM supplemented with 10 vol % FBS and 1 vol % ABAM for 5-10 days till plates reached confluence. Keratinocytes were initially cultured on collagen pre-coated plates in keratinocytes serum free medium (KSF) supplemented with bovine pituitary extract (BPE), Epidermal Growth Factor (EGF) and 10 vol % FBS for the first 24-48 hours. The media were then removed and KSF supplemented with BPE and EGF were added to the culture on 2 day interval for 7-10 day till cells reached confluence. This isolation and culturing protocol improved the cell viability and cell yield from the skin biopsy. It also helped in maximizing the number of keratinocytes that attach to the plates and ultimately proliferate. Both cells were cultured for 10 days until they reached confluence.

Four full thickness excisional wounds of 10×10 cm each were created on the back of pig model (n=6). The wounds were scanned using a hand-held laser scanner with a depth detector. Using Geomagic® software (Research Triangle Park, North Carolina), the wound area was carefully determined and measurements of surface area, volume and depth were determined.

Autologous and allogenic fibroblasts and keratinocytes, suspended in fibrinogen/collagen solution, were printed directly on two wounds. Fibroblasts were printed first and crosslinked with thrombin to form a gel layer, followed by delivering keratinocytes over the fibroblast layer. The remaining two wound groups received fibrinogen/collagen gel without cells and left untreated as controls. The animals were followed for up to 5 weeks and analyzed for wound healing, reepithelialization and contracture.

Figure 16:
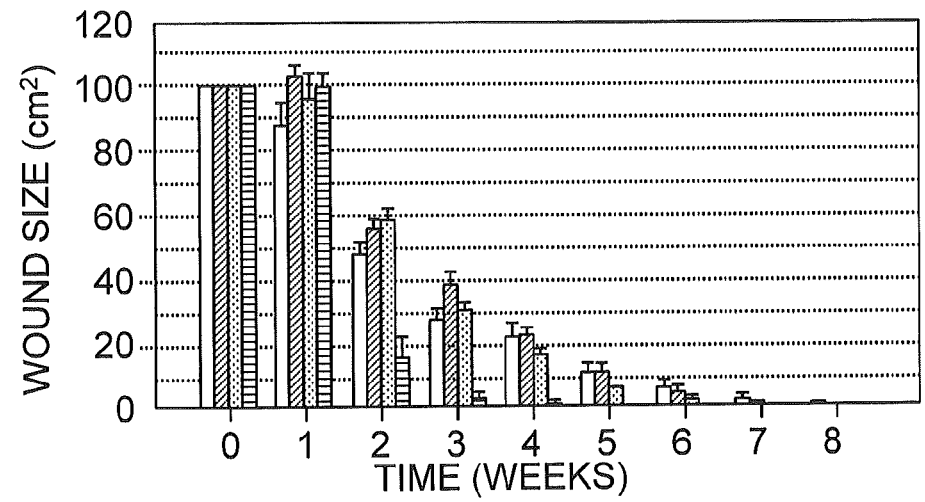
FIG. 16 presents data on wound size, contracture and re-epithelialization of untreated, matrix only, allogeneic and autologous treatments over an 8-week period.
Figure 16:
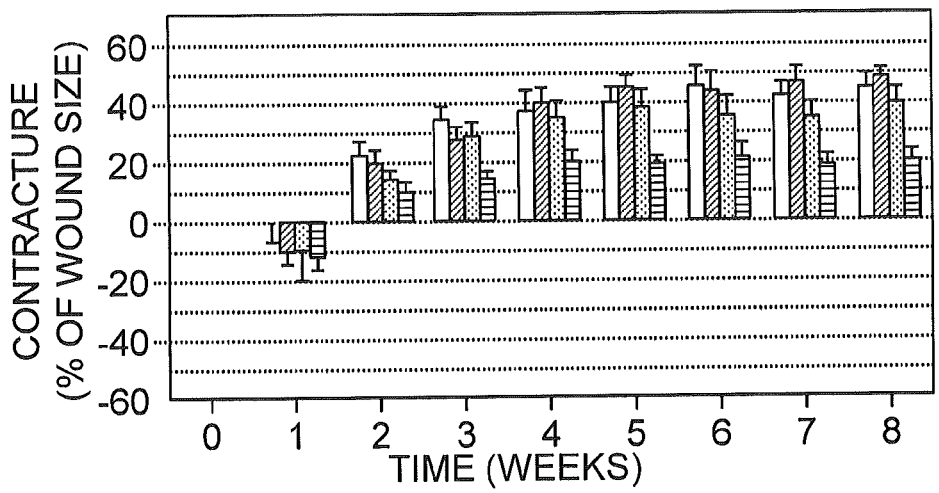
Figure 16:
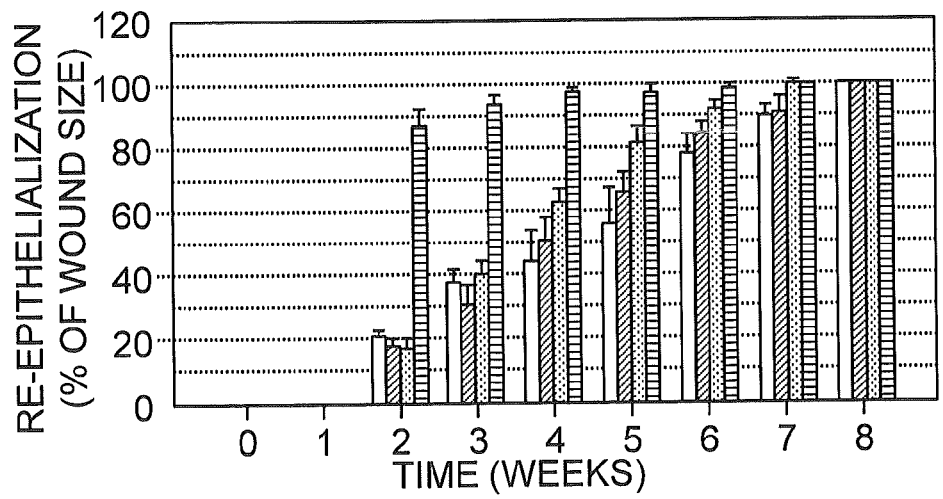

Results:

Wound healing was monitored over the 8 weeks of the study. Wounds received autologous treatments showed almost complete healing in 3 weeks compared to other treatments by the end of week 6 of the study. Wounds with autologous cells also showed an accelerated wound re-epithelialization and had almost 95% wound re-epithelialization by the third week of study. Wound contracture was minimal for autologous treatments throughout the study (<20% of the original wound size) as compared to the other treatments, which showed a progressive increase in contraction that exceeded 40% of the original wound size (FIG. 16). Wounds that received allogenic cells did not show notable differences with respect to wound size, re-epithelialization and contracture when compared to controls (untreated and matrix only).

Figure 17:
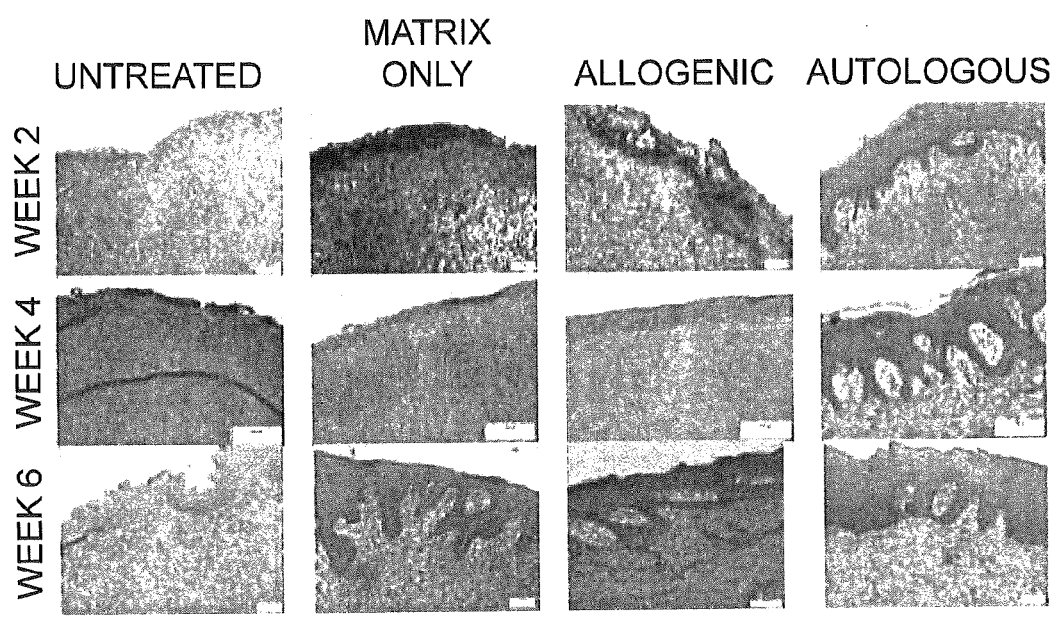
FIG. 17 shows H&E staining of skin biopsies taken from the center of the wound at week 2, 4 and 6, of untreated, matrix only, allogeneic and autologous treatments, to detect the formation of the epidermal and dermal layers.

Histological analyses (FIG. 17) showed a complete formation of epidermis and dermis layers within the first two weeks of study in the autologous treatments. Other treatments showed a formation of epidermis and dermis layer by week 6 of the study.

These results demonstrate the ability to regenerate skin within two weeks using autologous cells with minimal contraction and accelerated wound re-epithelialization.

The foregoing is illustrative of the present invention, and is not to be construed as limiting thereof. The invention is defined by the following claims, with equivalents of the claims to be included therein.

That which is claimed is:

1. A method of dispensing a composition onto a bodily surface of a patient in need thereof, comprising:
   (a) detecting said bodily surface with an optical detector to obtain three-dimensional coordinates thereof, wherein said optical detector further comprises a depth detector to account for movement of the patient;
   (b) processing the three-dimensional coordinates by:
       (i) interpreting the coordinates to form a model of the bodily surface;

(ii) transforming the model into a negative mold of the bodily surface, which mold is split into a plurality of Z-axis layers; and (iii) overlaying each of said Z-axis layers in the negative mold with a series of lines which represent coverage of the bodily surface, wherein said lines provide a path for a dispenser; and (c) dispensing the composition onto said bodily surface of said patient with said dispenser based upon said coordinates, wherein the dispensing step is carried out by:

(i) mixing fibroblast cells with a hydrogel to form a composition comprising fibroblast cells;

(ii) dispensing the composition comprising fibroblast cells onto the bodily surface;

(iii) crosslinking the composition comprising fibroblast cells to form a gel layer; and (iv) dispensing a composition comprising keratinocytes over the gel layer.

2. The method of claim 1, wherein the dispensing step (ii) is carried out not more than five minutes after said mixing step (i).

3. The method of claim 1, wherein said hydrogel comprises fibrinogen.

4. The method of claim 1, wherein said hydrogel comprises collagen.

5. The method of claim 1, wherein the composition comprising keratinocytes comprises a hydrogel.

6. The method of claim 5, wherein the keratinocytes is mixed in the hydrogel not more than five minutes prior to the dispensing step (iv).

7. The method of claim 1, wherein said fibroblast cells are delivered at a concentration of about 50,000 to 500,000 cells per cm$^2$.

8. The method of claim 1, wherein said keratinocytes are delivered at a concentration of about 50,000 to 500,000 cells per cm$^2$.

9. The method of claim 1, wherein said fibroblast cells and said keratinocytes are autologous with respect to said patient.

10. The method of claim 9, wherein said fibroblast cells are produced by obtaining cells from said patient and culturing said cells to form a cell culture.

11. The method of claim 9, wherein said keratinocytes are produced by obtaining cells from said patient and culturing said cells to form a cell culture.

12. The method of claim 1, wherein said optical detector is a hand-held scanner.

13. The method of claim 1, wherein the dispensing step (ii) or the dispensing step (iv) is carried out in a time of from 5 to 30 minutes.

14. The method of claim 1, wherein the dispensing step (ii) or the dispensing step (iv) is carried out by depositing drops of said composition along said path, wherein said drops have a volume of from 1 to 500 microliters.

15. The method of claim 14, wherein said drops have a volume of from 50 to 250 microliters.

16. The method of claim 1, wherein said composition comprises viable cells and wherein said dispensing step comprises forming a tissue.

17. The method of claim 16, wherein said tissue is skin tissue.

18. The method of claim 1, wherein said optical detector is a scanner.

19. The method of claim 1, wherein the Z-axis layers correspond to one or more tissue layers.

20. The method of claim 1, wherein said depth detector comprises a range camera that collects three-dimensional scene information from a continuously-projected light.

21. The method of claim 20, wherein said continuously-projected light is an infrared structured light.

22. The method of claim 1, wherein the three-dimensional coordinates are updated in real time during said dispensing.

* * * * *